(12) United States Patent
Riser

(10) Patent No.: US 8,518,395 B2
(45) Date of Patent: Aug. 27, 2013

(54) CCN3 PEPTIDES AND ANALOGS THEREOF FOR THERAPEUTIC USE

(75) Inventor: Bruce L. Riser, Kenosha, WI (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 13/079,693

(22) Filed: Apr. 4, 2011

(65) Prior Publication Data

US 2011/0250180 A1 Oct. 13, 2011

Related U.S. Application Data

(60) Provisional application No. 61/341,694, filed on Apr. 2, 2010.

(51) Int. Cl.
*A01N 63/00* (2006.01)
*A01N 65/00* (2009.01)
*A61K 38/00* (2006.01)

(52) U.S. Cl.
USPC .......................................... 424/93.7; 514/1.1

(58) Field of Classification Search
None
See application file for complete search history.

(56) References Cited

U.S. PATENT DOCUMENTS

| | | | |
|---|---|---|---|
| 2003/0059768 A1 | 3/2003 | Vernet et al. | |
| 2004/0009940 A1 | 1/2004 | Coleman et al. | |
| 2004/0191230 A1 | 9/2004 | Auclair et al. | |
| 2004/0224360 A1 | 11/2004 | Riser et al. | |
| 2006/0178332 A1 | 8/2006 | Riser | |
| 2007/0059314 A1* | 3/2007 | Plouet et al. | 424/146.1 |
| 2010/0004169 A1 | 1/2010 | Irvine et al. | |

FOREIGN PATENT DOCUMENTS

| | | | |
|---|---|---|---|
| EP | 1 382 347 | | 1/2004 |
| WO | WO2004/090109 A2 | | 10/2004 |
| WO | WO/2006/036962 | * | 4/2006 |
| WO | WO 2006/036962 | | 4/2006 |

OTHER PUBLICATIONS

Gupta et al. NOV (CCN3) functions as a regulator of human hematopoietic stem or progenitor cells. Science 2007, 316(5824):590-593; abstract.
Uniprot—Direct Submission P48745 (Mar. 2, 2010) [Retrived from the Internet Jul. 7, 2011: <http://www.uniprot.org/uniprot/P48745.txt?version-94>.
Perbal B., NOV and the CCN family of genes: structural and functional issues. *J. Clin. Pathol: Molecular Pathology* 54: 57-79, 2001.
Brigstock D. R., Regulation of angiogenesis and endothelial cell function by connective tissue growth factor and cystiene-rich 61 (CYR61). *Angiogensis* 5: 153-165, 2002.
Bradham MD et al, Connective tissue growth factor: a cysteine-rich mitogen secreted by human vascular endothelial cells is related to SCR-induced immediate early gene product CEF-10. *Journal of Cell Biology*, 114:1285-1294, 1991.
Tsai et al., Expression and function of CYR61, an angiogenic factor, in breast cancer cell lines and tumor biopsies. *Cancer Research* 60: 5603-5607, 2000.
Tsai et al., Expression and regulation of Cyr61 in human breast cancer cell lines. *Oncogene* 21: 964-973, 2002.
Sampath et al. Cyr61, a member of the CCN family, is required for MCF-7 cell proliferation: regulation by 17 beta-estradiol and overexpression in human breast cancer. *Endocrinology* 142: 2540-2548, 2001.
Sampath et al., Aberrant expression of Cyr 61, a member of the CCN family (i.e. CCN1), and dysregulation by 17 beta-estradiol and basic fibroblast growth factor in human uterine leiomyomas. *Journal of Clinical Endocrinology and Metabolism*, 86: 1707-1715, 2001.
Sampath et al, The angiogenic factor Cyr61 is induced by progestin R5020 and is necessary for mammary adenocarcinorma cell growth. *Endocrine*, 18: 147-159, 2002.
Xie et al., Breast cancer, Cyr61 is overexpressed, estrogen-inducible, and associated with more advanced disease. *Journal of Biological Chemistry*, 276: 14187-14194, 2001.
Xie et al., Elevated levels of connective tissue growth factor, WISP-1, and CYR61 in primary breast cancers associated with more advanced features. *Cancer Research*, 61: 8917-8923, 2001.
Rageh et al., Steroidal regulation of connective tissue growth factor (CCN2; CTGF) synthesis in the mouse uterus. *J. Clin. Pathol:Molecular Pathology*, 54: 338-346, 2001.
Cheon et al., A genomic approach to identify novel progesterone receptor regulated pathways in the uterus during implantation. *Molecular Endocrinology*, 16: 2853-2871, 2002.
Wandji et al., Messenger ribonucleic acids for MAC25 and connective tissue growth factor (CTGF) are inversely regulated during folliculogenesis and early luteogenesis. *Endocrinology*, 141: 2648-2657, 2000.
Slee et al., Differentiation-dependent expression of connective tissue growth factor and lysyl oxidase messenger ribonucleic acids in rat granulose cells. *Endocrinology*, 142: 1082-1089, 2001.
Harlow & Hillier, Connective tissue growth factor in the ovarian paracrine system. *Molecular and Cellular Endocrinology*, 187: 23-27, 2002.
Harlow et al., FSH and TGF-beta superfamily members regulate granulose cell connective tissue growth factor gene expression in vitro and in vivo. *Endocrinology*, 143: 3316-3325, 2002.
Liu et al., Gonodotrophins inhibit the expression of insulin-like growth binding protein-related protein-2 mRNA in cultured human granulose-luteal cells. *Molecular Human Reproduction*, 8: 136-141; 2002.

(Continued)

*Primary Examiner* — Cecilia J Tsang
*Assistant Examiner* — Sergio Coffa
(74) *Attorney, Agent, or Firm* — Joseph A. Fuchs; The Chicago Technology Law Group LLC

(57) ABSTRACT

The present invention provides a CCN3 peptide for treating a subject in need thereof having an amino acid sequence identified as CCNp37, CCNp38 (human), CCNp38 (mouse), a cysteine-substituted CCNp37, cysteine-substituted CCNp38 (human) or a cysteine-substituted CCNp38 (mouse).

6 Claims, 15 Drawing Sheets

(56) References Cited

OTHER PUBLICATIONS

Kyurkchiev S. et al., Potential cellular conformations of the CCN3 (NOV) protein. *Cellular Communication and Signaling*, 2: 9-18, 2004.

Li, C. L. et al., A role for CCN3 (NOV) in calcium signaling. *Journal of Clinical Pathology: Molecular Pathology*, 55: 250-261, 2002.

Dean R.G., Balding L., Candido R., Burns W.C., Cao Z., Twigg S.M., Burrell L,M. Connective tissue growth factor and cardiac fibrosis after myocardial infarction. *Journal of Histochemistry & Cytochemistry*. 53(10):1245-56, 2005.

Shi-wen X., Pennington D., Holmes A., Leask A., Bradham D., Beauchamp J.R., Fonseca C., du Bois R.M., Martin G.R., Black C.M., Abraham D.J. Autocrine overexpression of CTGF maintains fibrosis: RDA analysis of fibrosis genes in systemic sclerosis. *Experimental Cell Research*. 259(1):213-24, 2000.

Ozaki S., Sato Y., Yasoshima M., Harada K., Nakanuma Y. Diffuse expression of heparan sulfate proteoglycan and connective tissue growth factor in fibrous septa with many mast cells relate to unresolving hepatic fibrosis of congenital hepatic fibrosis. *Liver International*. 25(4):817-28, 2005.

Sakamoto N., Sugimura K., Kawashima H., Tsuchida K., Takemoto Y., Naganuma T., Tatsumi S., Nakatani T. Influence of glucose and inflammatory cytokines on TGF-beta1 and CTGF mRNA expressions in human peritoneal mesothelial cells. *International Journal of Molecular Medicine*. 15(6):907-11, 2005.

Zarrinkalam K.H., Stanley J.M., Gray J., Oliver N., Faull R.J. Connective tissue growth factor and its regulation in the peritoneal cavity of peritoneal dialysis patients. *Kidney International*. 64(1):331-8, 2003.

Riser, B. L. et al., Urinary CCN2 (CTGF) as a possible predictor of diabetic nephropathy: Preliminary report. *Kidney International*. 64: 451-458, 2003.

Wang S. Denichilo M. Brubaker C. Hirschberg R. Connective tissue growth factor in tubulointerstitial injury of diabetic nephropathy. *Kidney International*. 60(1):96-105, 2001.

Perbal B., J Cell Commun Signal, 2(1-2):Jun. 3-7, 2008.

Yeger et al., J Cell Commun Signal, 1(3-4): 159-164, Dec. 2007.

Brigstock (2003). J. Endocrinology, 178, 169-175.

Jeager et al. (2002) Am. J. Neurorad. 23, 200-207.

Perbal. (2003) Exert Rev Molec Diag. 3, 597-604.

\* cited by examiner

FIG. 2

ORIGINAL SEQUENCE - MOUSE CCN3 (NOV)

MSLFLRKRCLCLGFLLFHLLSQVSASLRCPSRCPPKCPSISPTCAPGVRSVLDGCSCCP
VCARQRGESCSEMRPCDQSSGLYCDRSADPNNQTGICMVPEGDNCVFDGVIYRNGEKFE
PNCQYFCTCRDGQIGCLPRCQLDVLLPGPDCPAPRKVAVPGECCEKWTCGSDEQGTQGT
LGGLALPAYRPEATVGVEVSDSSINCIEQTTEWSACSKSCGMGVSTRVTNRNRQCEMVK
QTRLCIVRPCEQEPEEVTDKKGKKCLRTKKSLKAIHLQFENCTSLYTYKPRFCGVCSDG
RCCTPHNTKTIQVEFQCLPGEIIKKPVMVIGTCTCYSNCPQNNEAFLQDLELKTSRGEI

MODIFIED SEQUENCE USED TO DESIGN PEPTIDES - SERINE
REPLACEMENT OF CYSTEINE

MSLFLRKRSLSLGFLLFHLLSQVSASLRSPSRSPPKSPSISPTSAPGVRSVLDGSSSSP
VSARQRGESSSEMRPSDQSSGLYSDRSADPNNQTGISMVPEGDNSVFDGVIYRNGEKFE
PNSQYFSTSRDGQIGSLPRSQLDVLLPGPDSPAPRKVAVPGESSEKWTSGSDEQGTQGT
LGGLALPAYRPEATVGVEVSDSSINSIEQTTEWSASSKSSGMGVSTRVTNRNRQSEMVK
QTRLSIVRPSEQEPEEVTDKKGKKSLRTKKSLKAIHLQFENSTSLYTYKPRFSGVSSDG
RSSTPHNTKTIQVEFQSLPGEIIKKPVMVIGTSTSYSNSPQNNEAFLQDLELKTSRGEI

FIG. 3

| | | |
|---|---|---|
| MSLFLRKRSLSLGFL | 1 | |
| SLGFLLFHLLSQVSA | 2 | |
| SQVSASLRSPSRSPP | 3 | |
| RSPSRSPPKSPSISPTSA | 4 | |
| SPTSAPGVRSVLDGS | 5 | |
| VLDGSSSSPVSARQR | 6 | |
| SARQRGESSSEMRPS | 7 | |
| EMRPSDQSSGLYSDR | 8 | |
| LYSDRSADPNNQTGI | 9 | |
| NQTGISMVPEGDNSV | 10 | |
| GDNSVFDGVIYRNGE | 11 | |
| YRNGEKFEPNSQYF | 12 | |
| SQYFSTSRDGQIGSL | 13 | |
| QIGSLPRSQLDVLLP | 14 | |
| DVLLPGPDSPAPRKV | 15 | |
| APRKVAVPGESSEK | 16 | |
| SSEKWTSGSDEQGTQGT | 17 | |
| DEQGTQGTLGGIALP | 18 | |
| LALPAYRPEATVGV | 19 | |
| ATVGVEVSDSSINSI | 20 | |
| SINSIEQTTEWSASS | 21 | |
| WSASSKSSGMGVSTR | 22 | |
| GVSTRVTNRQSEM | 23 | |
| RQSEMVKQTRLSIVR | 24 | |
| LSIVRPSEQEPEEVT | 25 | |
| PEEVTDKKGKKSLRT | 26 | |
| KSLRTKKSLKAIHLQ | 27 | |
| AIHLQFENSTLYTY | 28 | |
| SLYTYKPRFSGVSSD | 29 | |
| GVSSDGRSSTPHNTK | 30 | |
| PHNTKTIQVEFQSLP | 31 | |
| FQSLPGEIIKKPVMV | 32 | |
| KPVMVIGTSTSYSNS | 33 | |
| SNSPQNNEAFIQDL | 34 | |
| AFLQDLELKTSRGEI | 35 | |
| KQTRLSIVRPSEQ | 36 | (PART OF #23) |
| FSGVSSDGRSSTPH | 37 | (PART OF #29 AND #30) |
| SDRSADPNNQTGIS | 38 | (PART OF #8 AND #9) |
| QTTEW SASSKSSGMG | 39 | (PART OF #s 20,21,22) |
| SSKSSGMGVSTRVTN | 40 | (PART OF #s 20,21,22) |

FIG. 4

CTGF / CCN2  1—27  97—101  167  199—243  256—330  349
NOV / CCN3   1—29  100—104  170  202—246  258—332  351

RESULTS OF SIM WITH

SEQUENCE 1: HCCN2 (349 RESIDUES) NM 001901
SEQUENCE 2: HCCN3 (357 RESIDUES) NM 002514

53.2% IDENTITY IN 325 RESIDUES OVERLAP; SCORE: 995.0; GAP FREQUENCY: 1.2%

```
HCCN2   15  VLLALCSRPAVGQNCSGPC--RCPDEPAPRCPAGVSLVLDGCGCCRVCAKQLGELCTERD
HCCN3   21  LLLHLLGQVAATQRCPPQCPGRCPATP-PTCAPGVRAVLDGCSCCLVCARQRGESCSDIE
                 *   *      *  ***** *** * ****** ***** *****  **   *

HCCN2   73  PCDPHKGLFCDFGSPANRKIGVCTAKDGAPCIFGGTVYRSGESFQSSCKYQCTCLDGAVG
HCCN3   80  PCDESSGLYCDRSADPSNQTGICTAVEGDNCVEDGVIYRSGEKFQPSCKFQCTCRDGQIG
            ***   **  **   *  * * *** *   *  *  * *****  * *** ****  * *

HCCN2  133  CMPLCSMDVRLPSPDCPFPRRVKLPGKCCEEWVCDEPKDQTVVGPALAAYRLEDTFGPDP
HCCN3  140  CVPRCQLDVLLPEPNCPAPRKVEVPGECCEKWICGPDEEDSLGGITLAAYRPEATLGVEV

HCCN2  193  TMIRANCLVQTTEWSACSKTCGMGISTRVTNDNASCRLEKQSRLCMVRPCEADLEENI-K
HCCN3  200  SDSSVNCIEQTTEWTACSKSCGMGFSTRVTNRNRQCEMLKQTRLCMVRPCEQEPEQPTDK

HCCN2  252  KGKKCIRTPKISKPIKFSLSGCTSMKTYRAKFCGVCTDGRCCTPHRTTTLEVEFKCPDGE
HCCN3  260  KGKKCLRTKKSLKAIHLQFKNCTSLHTYKPRFCGVCSDGPCCTPHNTKTIQAEFQCSPGQ

HCCN2  312  VMKKNMMFIKTCACHYNCPGDNDIF
HCCN3  320  IVKKPVMVIGTCTCHTNCPKNNEAF
```

58.3% IDENTITY IN 12 RESIDUES OVERLAP; SCORE: 41.0; GAP FREQUENCY: 0.0%

SHOWS REGIONS ON THE CCN3 SEQUENCE CHOSEN- ALL CYSTEINES WERE REPLACED BY SERINES (AS SHOWN). DOTTED LINE SHOWS OVERLAPPING PEPTIDES MADE. BOLDED SHOWS SEQUENCE OF PEPTIDES DESIGNED FOR SPECIFIC REGIONS, ALSO OVERLAPPING WITH OTHERS MADE.

FIG. 6

FROM THE THROMBOSPONDIN LIKE (TSP) ELEMENT, OF MOUSE CCN3:

(CCN3p 39) QTTEWSACSKSCGM   APPROX 90% HOMOLOGY, SEQUENCE APPROX 206-220

(CCN3p 40) CSKSCGMGVSTRVTN   APPROX 90% HOMOLOGY, SEQUENCE APPROX 213-227

(CCN3p 36) KQTRLCIVRPCEQ   APPROX 50% HOMOLOGY, SEQUENCE APPROX 236-248

FROM THE C-TERM ELEMENT, MOUSE CCN3:

(CCN3p 37) FCGVCSDGRCCTPH   APPROX 92.9% HOMOLOGY, SEQUENCE APPROX 289-302

FROM INSULIN-LIKE GROWTH FACTOR BINDING DOMAIN (IGFBD) ELEMENT, MOUSE CCN3:

(CCN3p 38) CDRSADPNNQTGIC   APPROX 28% HOMOLOGY, SEQUENCE APPROX 84-98

FIG. 7A

PEPTIDES MADE AND TESTED: (WITH ANY CYSTEINES [C] FOUND IN THE NATURAL SEQUENCE REPLACED WITH SERINES [S])

CCN3p37    ACETYL-FSGVSSDGRSSTPH-NH2
CCN3p38    ACETYL-SDRSADPNNQTGIS-NH2

FIG. 7B

EQUIVALENT NATURAL SEQUENCE: (i.e. WITH CYSTEINES)

CCN3p37    (HUMAN & MOUSE)    FCGVCSDGRCCTPH    (IS THE SAME IN MOUSE AND HUMANS)
CCN3p38    (MOUSE)            CDRSADPNNQTGIC
CCN3p38    (HUMAN)            CDRSADPSNQTGIC    (CCN3) HUMAN IS ONE AA DIFFERENT FROM MOUSE

\* BOLDED LETTER (AA) INDICATES THAT THE SEQUENCE IS DIFFERENT IN THIS POSITION THAN THAT MADE AND TESTED.

FIG. 7C

NATURAL SEQUENCE HUMAN CCN2 AND CCN3 AT THE REGIONS SELECTED FOR CCN3p37 AND CCN3p38 W/ CYSTEINES INTACT

FCGVCTDGRCCTPH     CCN2 HUMAN (BOLDED SHOWING SEQUENCE DIFFERENCES WITH CCN3)
FCGVCSDGRCCTPH     CCN3p37 HUMAN W/ CYSTEINES INTACT

CDFGSPANRKIGVC     CCN2 HUMAN (BOLDED SHOWING SEQUENCE DIFFERENCES WITH CCN3)
CDRSADPSNQTGIC     CCN3p38 HUMAN W/ CYSTEINES INTACT

\* NOTE THE SEQUENCE FOR CCN2 IS OFTEN QUITE DIFFERENT FROM THAT OF CCN3 EVEN UNDER OPTIMAL ALIGNMENT.

FIG. 7D

NATURAL SEQUENCE MOUSE CCN2 AND CCN3 AT THE REGIONS SELECTED FOR CCN3p37 AND CCN3p38 W/ CYSTEINES INTACT

FCGVCTDGRCCTPH     CCN2 MOUSE (BOLDED SHOWING SEQUENCE DIFFERENCES WITH CCN3)
FCGVCSDGRCCTPH     CCN3p37 MOUSE W/ CYSTEINES INTACT (SAME AS ABOVE-HUMAN)

CDFGSPANRKIGVC     CCN2 MOUSE (BOLDED SHOWING SEQUENCE DIFFERENCES WITH CCN3)
CDRSADPNNQTGIC     CCN3 CCN3p38 MOUSE W/ CYSTEINES INTACT (1 AA DIFFERENT FROM ABOVE-HUMAN AT CCN3)

\* NOTE THE SEQUENCE FOR CCN2 IS OFTEN QUITE DIFFERENT FROM THAT OF CCN3 EVEN UNDER OPTIMAL ALIGNMENT.

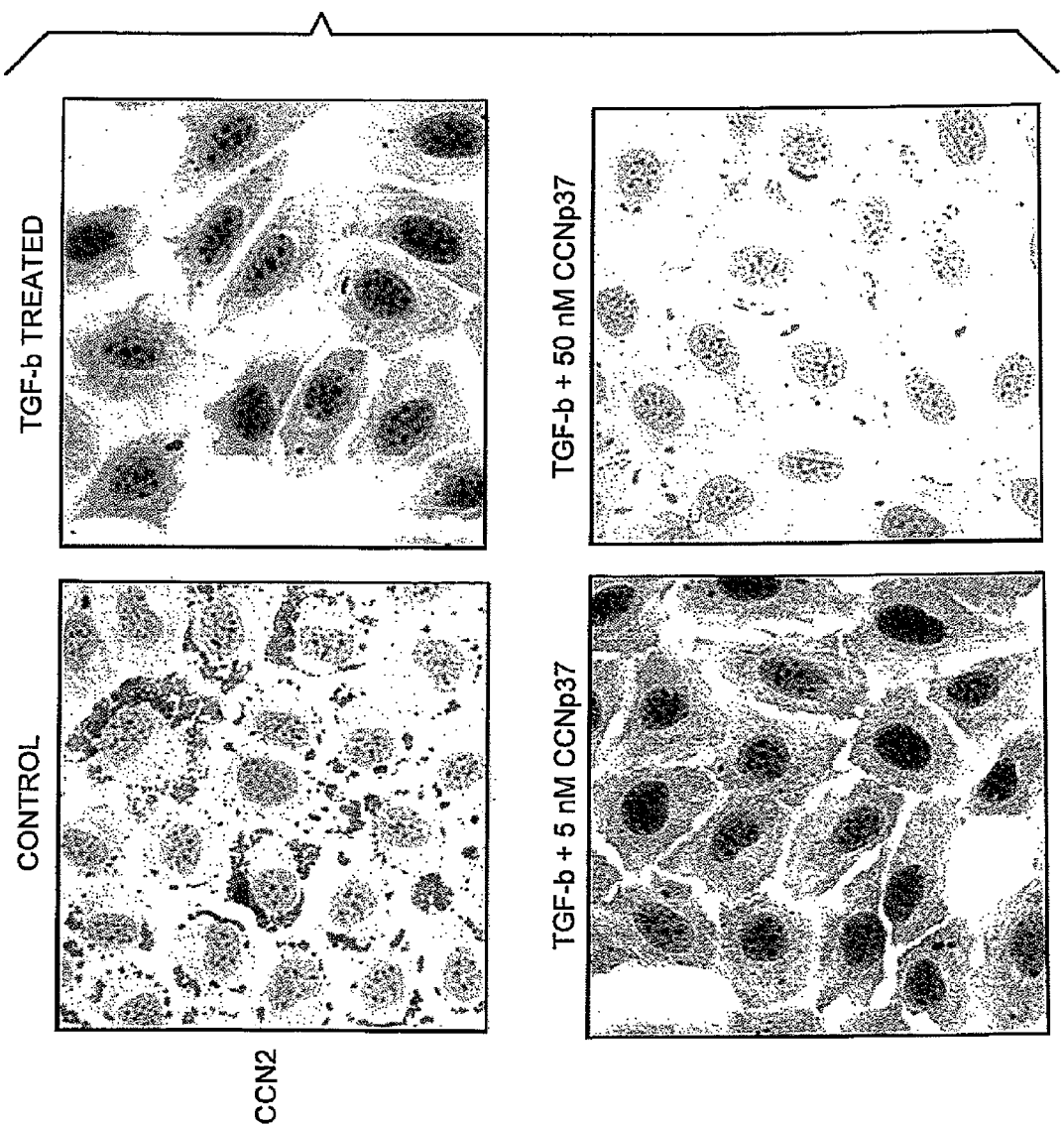

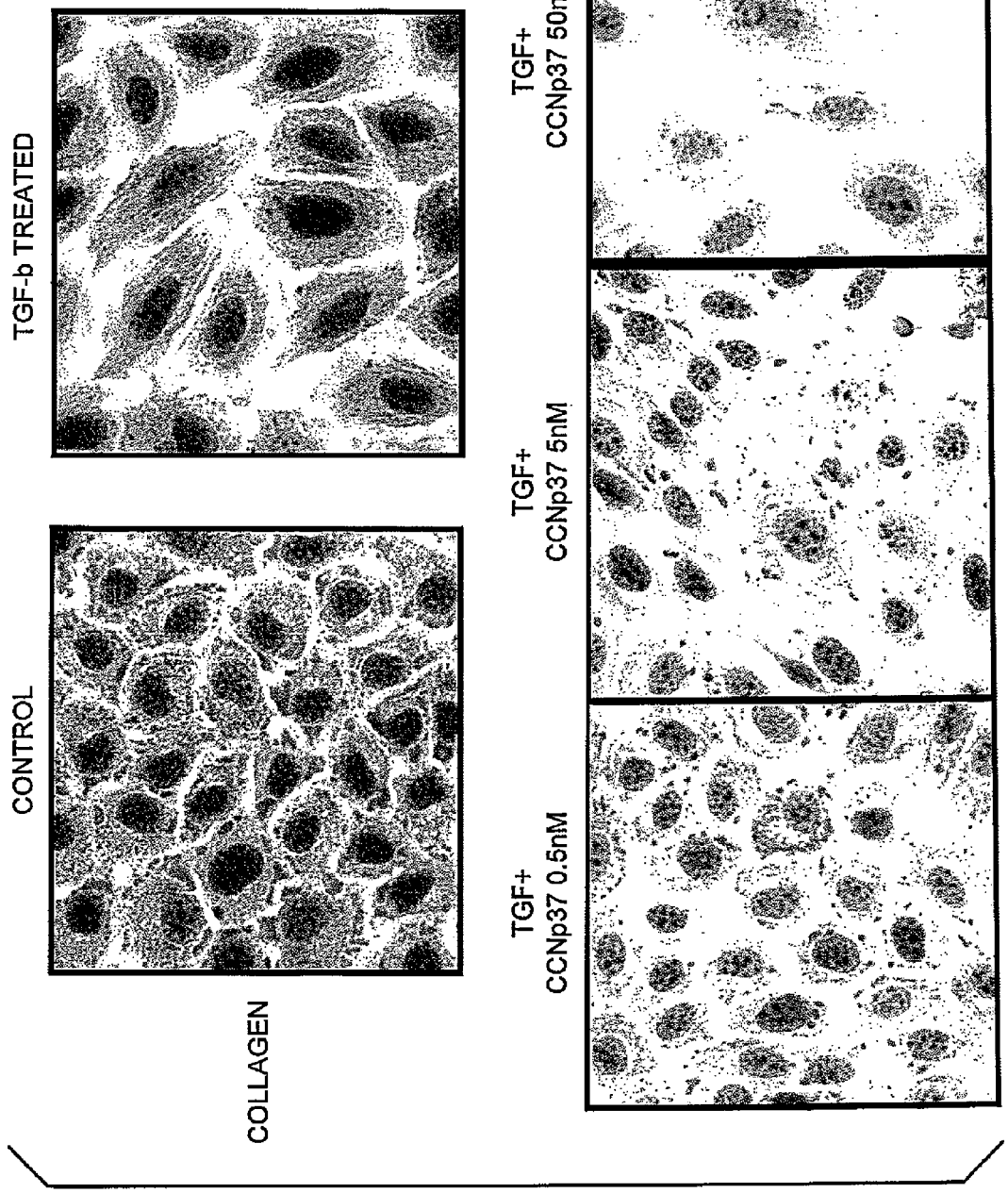

SEQUENCE LISTING

```
<160> NUMBER OF SEQ ID NOS: 55

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Ser Leu Phe Leu Arg Lys Arg Ser Leu Ser Leu Gly Phe Leu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Ser Leu Gly Phe Leu Leu Phe His Leu Leu Ser Gln Val Ser Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Gln Val Ser Ala Ser Leu Arg Ser Pro Ser Arg Ser Pro Pro
1               5                   10                  15

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Pro Ser Arg Ser Pro Pro Lys Ser Pro Ser Ile Ser Pro Thr
1               5                   10                  15

Ser Ala

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Pro Thr Ser Ala Pro Gly Val Arg Ser Val Leu Asp Gly Ser
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Leu Asp Gly Ser Ser Ser Ser Pro Val Ser Ala Arg Gln Arg
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ala Arg Gln Arg Gly Glu Ser Ser Ser Glu Met Arg Pro Ser
1               5                   10                  15

<210> SEQ ID NO 8
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Met Arg Pro Ser Asp Gln Ser Ser Gly Leu Tyr Ser Asp Arg
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Tyr Ser Asp Arg Ser Ala Asp Pro Asn Asn Gln Thr Gly Ile
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Gln Thr Gly Ile Ser Met Val Pro Glu Gly Asp Asn Ser Val
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Asp Asn Ser Val Phe Asp Gly Val Ile Tyr Arg Asn Gly Glu
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Arg Asn Gly Glu Lys Phe Glu Pro Asn Ser Gln Tyr Phe
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gln Tyr Phe Ser Thr Ser Arg Asp Gly Gln Ile Gly Ser Leu
```

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ile Gly Ser Leu Pro Arg Ser Gln Leu Asp Val Leu Leu Pro
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Val Leu Leu Pro Gly Pro Asp Ser Pro Ala Pro Arg Lys Val
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Pro Arg Lys Val Ala Val Pro Gly Glu Ser Ser Glu Lys
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ser Glu Lys Trp Thr Ser Gly Ser Asp Glu Gln Gly Thr Gln Gly
1               5                   10                  15

Thr

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Glu Gln Gly Thr Gln Gly Thr Leu Gly Gly Leu Ala Leu Pro
1               5                   10                  15

<210> SEQ ID NO 19
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 19

Leu Ala Leu Pro Ala Tyr Arg Pro Glu Ala Thr Val Gly Val
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Thr Val Gly Val Glu Val Ser Asp Ser Ser Ile Asn Ser Ile
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Ile Asn Ser Ile Glu Gln Thr Thr Glu Trp Ser Ala Ser Ser
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Ser Ala Ser Ser Lys Ser Ser Gly Met Gly Val Ser Thr Arg
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Val Ser Thr Arg Val Thr Asn Arg Asn Arg Gln Ser Glu Met
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Gln Ser Glu Met Val Lys Gln Thr Arg Leu Ser Ile Val Arg
1               5                   10                  15

<210> SEQ ID NO 25
```

-continued

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Ser Ile Val Arg Pro Ser Glu Gln Glu Pro Glu Glu Val Thr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Glu Glu Val Thr Asp Lys Lys Gly Lys Lys Ser Leu Arg Thr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Ser Leu Arg Thr Lys Lys Ser Leu Lys Ala Ile His Leu Gln
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ile His Leu Gln Phe Glu Asn Ser Thr Ser Leu Tyr Thr Tyr
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Leu Tyr Thr Tyr Lys Pro Arg Phe Ser Gly Val Ser Ser Asp
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Val Ser Ser Asp Gly Arg Ser Ser Thr Pro His Asn Thr Lys
```

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 31

Pro His Asn Thr Lys Thr Ile Gln Val Glu Phe Gln Ser Leu Pro
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 32

Phe Gln Ser Leu Pro Gly Glu Ile Ile Lys Lys Pro Val Met Val
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 33

Lys Pro Val Met Val Ile Gly Thr Ser Thr Ser Tyr Ser Asn Ser
1               5                   10                  15

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 34

Ser Asn Ser Pro Gln Asn Asn Glu Ala Phe Leu Gln Asp Leu
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 35

Ala Phe Leu Gln Asp Leu Glu Leu Lys Thr Ser Arg Gly Glu Ile
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
    peptide -continued

```
<400> SEQUENCE: 36

Lys Gln Thr Arg Leu Ser Ile Val Arg Pro Ser Glu Gln
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Phe Ser Gly Val Ser Ser Asp Gly Arg Ser Ser Thr Pro His
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Asp Arg Ser Ala Asp Pro Asn Asn Gln Thr Gly Ile Ser
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Thr Thr Glu Trp Ser Ala Ser Ser Lys Ser Ser Gly Met Gly
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Ser Lys Ser Ser Gly Met Gly Val Ser Thr Arg Val Thr Asn
1               5                   10                  15

<210> SEQ ID NO 41
<211> LENGTH: 354
<212> TYPE: PRT
<213> ORGANISM: Mus sp.

<400> SEQUENCE: 41

Met Ser Leu Phe Leu Arg Lys Arg Cys Leu Cys Leu Gly Phe Leu Leu
1               5                   10                  15

Phe His Leu Leu Ser Gln Val Ser Ala Ser Leu Arg Cys Pro Ser Arg
                20                  25                  30

Cys Pro Pro Lys Cys Pro Ser Ile Ser Pro Thr Cys Ala Pro Gly Val
            35                  40                  45

Arg Ser Val Leu Asp Gly Cys Ser Cys Cys Pro Val Cys Ala Arg Gln
```

```
            50                  55                  60
Arg Gly Glu Ser Cys Ser Glu Met Arg Pro Cys Asp Gln Ser Ser Gly
 65                  70                  75                  80

Leu Tyr Cys Asp Arg Ser Ala Asp Pro Asn Asn Gln Thr Gly Ile Cys
                 85                  90                  95

Met Val Pro Glu Gly Asp Asn Cys Val Phe Asp Gly Val Ile Tyr Arg
            100                 105                 110

Asn Gly Glu Lys Phe Glu Pro Asn Cys Gln Tyr Phe Thr Cys Arg
        115                 120                 125

Asp Gly Gln Ile Gly Cys Leu Pro Arg Cys Gln Leu Asp Val Leu Leu
        130                 135                 140

Pro Gly Pro Asp Cys Pro Ala Pro Arg Lys Val Ala Val Pro Gly Glu
145                 150                 155                 160

Cys Cys Glu Lys Trp Thr Cys Gly Ser Asp Glu Gln Gly Thr Gln Gly
                165                 170                 175

Thr Leu Gly Gly Leu Ala Leu Pro Ala Tyr Arg Pro Glu Ala Thr Val
            180                 185                 190

Gly Val Glu Val Ser Asp Ser Ser Ile Asn Cys Ile Glu Gln Thr Thr
        195                 200                 205

Glu Trp Ser Ala Cys Ser Lys Ser Cys Gly Met Gly Val Ser Thr Arg
    210                 215                 220

Val Thr Asn Arg Asn Arg Gln Cys Glu Met Val Lys Gln Thr Arg Leu
225                 230                 235                 240

Cys Ile Val Arg Pro Cys Glu Gln Glu Pro Glu Glu Val Thr Asp Lys
                245                 250                 255

Lys Gly Lys Lys Cys Leu Arg Thr Lys Lys Ser Leu Lys Ala Ile His
            260                 265                 270

Leu Gln Phe Glu Asn Cys Thr Ser Leu Tyr Thr Tyr Lys Pro Arg Phe
        275                 280                 285

Cys Gly Val Cys Ser Asp Gly Arg Cys Cys Thr Pro His Asn Thr Lys
        290                 295                 300

Thr Ile Gln Val Glu Phe Gln Cys Leu Pro Gly Glu Ile Ile Lys Lys
305                 310                 315                 320

Pro Val Met Val Ile Gly Thr Cys Thr Cys Tyr Ser Asn Cys Pro Gln
                325                 330                 335

Asn Asn Glu Ala Phe Leu Gln Asp Leu Glu Leu Lys Thr Ser Arg Gly
            340                 345                 350

Glu Ile

<210> SEQ ID NO 42
<211> LENGTH: 354
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Ser Leu Phe Leu Arg Lys Arg Ser Leu Ser Leu Gly Phe Leu Leu
 1               5                  10                  15

Phe His Leu Leu Ser Gln Val Ser Ala Ser Leu Arg Ser Pro Ser Arg
                20                  25                  30

Ser Pro Pro Lys Ser Pro Ser Ile Ser Pro Thr Ser Ala Pro Gly Val
            35                  40                  45

Arg Ser Val Leu Asp Gly Ser Ser Ser Pro Val Ser Ala Arg Gln
        50                  55                  60
```

Arg Gly Glu Ser Ser Glu Met Arg Pro Ser Asp Gln Ser Gly
65                  70                  75                  80

Leu Tyr Ser Asp Arg Ser Ala Asp Pro Asn Asn Gln Thr Gly Ile Ser
                85                  90                  95

Met Val Pro Glu Gly Asp Asn Ser Val Phe Asp Gly Val Ile Tyr Arg
                100                 105                 110

Asn Gly Glu Lys Phe Glu Pro Asn Ser Gln Tyr Phe Ser Thr Ser Arg
                115                 120                 125

Asp Gly Gln Ile Gly Ser Leu Pro Arg Ser Gln Leu Asp Val Leu Leu
                130                 135                 140

Pro Gly Pro Asp Ser Pro Ala Pro Arg Lys Val Ala Val Pro Gly Glu
145                 150                 155                 160

Ser Ser Glu Lys Trp Thr Ser Gly Ser Asp Glu Gln Gly Thr Gln Gly
                165                 170                 175

Thr Leu Gly Gly Leu Ala Leu Pro Ala Tyr Arg Pro Glu Ala Thr Val
                180                 185                 190

Gly Val Glu Val Ser Asp Ser Ile Asn Ser Ile Glu Gln Thr Thr
                195                 200                 205

Glu Trp Ser Ala Ser Ser Lys Ser Ser Gly Met Gly Val Ser Thr Arg
210                 215                 220

Val Thr Asn Arg Asn Arg Gln Ser Glu Met Val Lys Gln Thr Arg Leu
225                 230                 235                 240

Ser Ile Val Arg Pro Ser Glu Gln Pro Glu Glu Val Thr Asp Lys
                245                 250                 255

Lys Gly Lys Lys Ser Leu Arg Thr Lys Lys Ser Leu Lys Ala Ile His
                260                 265                 270

Leu Gln Phe Glu Asn Ser Thr Ser Leu Tyr Thr Tyr Lys Pro Arg Phe
                275                 280                 285

Ser Gly Val Ser Ser Asp Gly Arg Ser Ser Thr Pro His Asn Thr Lys
                290                 295                 300

Thr Ile Gln Val Glu Phe Gln Ser Leu Pro Gly Glu Ile Ile Lys Lys
305                 310                 315                 320

Pro Val Met Val Ile Gly Thr Ser Thr Ser Tyr Ser Asn Ser Pro Gln
                325                 330                 335

Asn Asn Glu Ala Phe Leu Gln Asp Leu Glu Leu Lys Thr Ser Arg Gly
                340                 345                 350

Glu Ile

<210> SEQ ID NO 43
<211> LENGTH: 322
<212> TYPE: PRT
<213> ORGANISM: Homo sapiens

<400> SEQUENCE: 43

Val Leu Leu Ala Leu Cys Ser Arg Pro Ala Val Gly Gln Asn Cys Ser
1               5                   10                  15

Gly Pro Cys Arg Cys Pro Asp Glu Pro Ala Pro Arg Cys Pro Ala Gly
                20                  25                  30

Val Ser Leu Val Leu Asp Gly Cys Gly Cys Cys Arg Val Cys Ala Lys
                35                  40                  45

Gln Leu Gly Glu Leu Cys Thr Glu Arg Asp Pro Cys Asp Pro His Lys
                50                  55                  60

Gly Leu Phe Cys Asp Phe Gly Ser Pro Ala Asn Arg Lys Ile Gly Val
65                  70                  75                  80

```
Cys Thr Ala Lys Asp Gly Ala Pro Cys Ile Phe Gly Thr Val Tyr
            85                  90                  95

Arg Ser Gly Glu Ser Phe Gln Ser Ser Cys Lys Tyr Gln Cys Thr Cys
                100                 105                 110

Leu Asp Gly Ala Val Gly Cys Met Pro Leu Cys Ser Met Asp Val Arg
            115                 120                 125

Leu Pro Ser Pro Asp Cys Pro Phe Pro Arg Arg Val Lys Leu Pro Gly
        130                 135                 140

Lys Cys Cys Glu Glu Trp Val Cys Asp Glu Pro Lys Asp Gln Thr Val
145                 150                 155                 160

Val Gly Pro Ala Leu Ala Ala Tyr Arg Leu Glu Asp Thr Phe Gly Pro
                165                 170                 175

Asp Pro Thr Met Ile Arg Ala Asn Cys Leu Val Gln Thr Thr Glu Trp
            180                 185                 190

Ser Ala Cys Ser Lys Thr Cys Gly Met Gly Ile Ser Thr Arg Val Thr
                195                 200                 205

Asn Asp Asn Ala Ser Cys Arg Leu Glu Lys Gln Ser Arg Leu Cys Met
    210                 215                 220

Val Arg Pro Cys Glu Ala Asp Leu Glu Glu Asn Ile Lys Lys Gly Lys
225                 230                 235                 240

Lys Cys Ile Arg Thr Pro Lys Ile Ser Lys Pro Ile Lys Phe Glu Leu
            245                 250                 255

Ser Gly Cys Thr Ser Met Lys Thr Tyr Arg Ala Lys Phe Cys Gly Val
                260                 265                 270

Cys Thr Asp Gly Arg Cys Cys Thr Pro His Arg Thr Thr Thr Leu Pro
            275                 280                 285

Val Glu Phe Lys Cys Pro Asp Gly Glu Val Met Lys Lys Asn Met Met
        290                 295                 300

Phe Ile Lys Thr Cys Ala Cys His Tyr Asn Cys Pro Gly Asp Asn Asp
305                 310                 315                 320

Ile Phe

<210> SEQ ID NO 44
<211> LENGTH: 324
<212> TYPE: PRT
<213> ORGANISM: Homo sapiens

<400> SEQUENCE: 44

Leu Leu Leu His Leu Leu Gly Gln Val Ala Ala Thr Gln Arg Cys Pro
1               5                   10                  15

Pro Gln Cys Pro Gly Arg Cys Pro Ala Thr Pro Pro Thr Cys Ala Pro
                20                  25                  30

Gly Val Arg Ala Val Leu Asp Gly Cys Ser Cys Cys Leu Val Cys Ala
            35                  40                  45

Arg Gln Arg Gly Glu Ser Cys Ser Asp Leu Glu Pro Cys Asp Glu Ser
    50                  55                  60

Ser Gly Leu Tyr Cys Asp Arg Ser Ala Asp Pro Ser Asn Gln Thr Gly
65                  70                  75                  80

Ile Cys Thr Ala Val Glu Gly Asp Asn Cys Val Phe Asp Gly Val Ile
            85                  90                  95

Tyr Arg Ser Gly Glu Lys Phe Gln Pro Ser Cys Lys Phe Gln Cys Thr
                100                 105                 110

Cys Arg Asp Gly Gln Ile Gly Cys Val Pro Arg Cys Gln Leu Asp Val
            115                 120                 125

Leu Leu Pro Glu Pro Asn Cys Pro Ala Pro Arg Lys Val Glu Val Pro
```

```
            130                 135                 140
Gly Glu Cys Cys Glu Lys Trp Ile Cys Gly Pro Asp Glu Asp Ser
145                 150                 155                 160

Leu Gly Gly Leu Thr Leu Ala Ala Tyr Arg Pro Glu Ala Thr Leu Gly
                165                 170                 175

Val Glu Val Ser Asp Ser Ser Val Asn Cys Ile Glu Gln Thr Thr Glu
                180                 185                 190

Trp Thr Ala Cys Ser Lys Ser Cys Gly Met Gly Phe Ser Thr Arg Val
                195                 200                 205

Thr Asn Arg Asn Arg Gln Cys Glu Met Leu Lys Gln Thr Arg Leu Cys
            210                 215                 220

Met Val Arg Pro Cys Glu Gln Glu Pro Glu Gln Pro Thr Asp Lys Lys
225                 230                 235                 240

Gly Lys Lys Cys Leu Arg Thr Lys Lys Ser Leu Lys Ala Ile His Leu
                245                 250                 255

Gln Phe Lys Asn Cys Thr Ser Leu His Thr Tyr Lys Pro Arg Phe Cys
                260                 265                 270

Gly Val Cys Ser Asp Gly Arg Cys Cys Thr Pro His Asn Thr Lys Thr
                275                 280                 285

Ile Gln Ala Glu Phe Gln Cys Ser Pro Gly Gln Ile Val Lys Lys Pro
            290                 295                 300

Val Met Val Ile Gly Thr Cys Thr Cys His Thr Asn Cys Pro Lys Asn
305                 310                 315                 320

Asn Glu Ala Phe

<210> SEQ ID NO 45
<211> LENGTH: 14
<212> TYPE: PRT
<213> ORGANISM: Mus sp.

<400> SEQUENCE: 45

Gln Thr Thr Glu Trp Ser Ala Cys Ser Lys Ser Cys Gly Met
1               5                   10

<210> SEQ ID NO 46
<211> LENGTH: 15
<212> TYPE: PRT
<213> ORGANISM: Mus sp.

<400> SEQUENCE: 46

Cys Ser Lys Ser Cys Gly Met Gly Val Ser Thr Arg Val Thr Asn
1               5                   10                  15

<210> SEQ ID NO 47
<211> LENGTH: 13
<212> TYPE: PRT
<213> ORGANISM: Mus sp.

<400> SEQUENCE: 47

Lys Gln Thr Arg Leu Cys Ile Val Arg Pro Cys Glu Gln
1               5                   10

<210> SEQ ID NO 48
<211> LENGTH: 14
<212> TYPE: PRT
<213> ORGANISM: Mus sp.

<400> SEQUENCE: 48

Phe Cys Gly Val Cys Ser Asp Gly Arg Cys Cys Thr Pro His
1               5                   10
```

-continued

```
<210> SEQ ID NO 49
<211> LENGTH: 14
<212> TYPE: PRT
<213> ORGANISM: Mus sp.

<400> SEQUENCE: 49

Cys Asp Arg Ser Ala Asp Pro Asn Asn Gln Thr Gly Ile Cys
1               5                   10

<210> SEQ ID NO 50
<211> LENGTH: 14
<212> TYPE: PRT
<213> ORGANISM: Homo sapiens

<400> SEQUENCE: 50

Phe Cys Gly Val Cys Ser Asp Gly Arg Cys Cys Thr Pro His
1               5                   10

<210> SEQ ID NO 51
<211> LENGTH: 14
<212> TYPE: PRT
<213> ORGANISM: Homo sapiens

<400> SEQUENCE: 51

Cys Asp Arg Ser Ala Asp Pro Ser Asn Gln Thr Gly Ile Cys
1               5                   10

<210> SEQ ID NO 52
<211> LENGTH: 14
<212> TYPE: PRT
<213> ORGANISM: Homo sapiens

<400> SEQUENCE: 52

Phe Cys Gly Val Cys Thr Asp Gly Arg Cys Cys Thr Pro His
1               5                   10

<210> SEQ ID NO 53
<211> LENGTH: 14
<212> TYPE: PRT
<213> ORGANISM: Homo sapiens

<400> SEQUENCE: 53

Cys Asp Phe Gly Ser Pro Ala Asn Arg Lys Ile Gly Val Cys
1               5                   10

<210> SEQ ID NO 54
<211> LENGTH: 14
<212> TYPE: PRT
<213> ORGANISM: Mus sp.

<400> SEQUENCE: 54

Phe Cys Gly Val Cys Thr Asp Gly Arg Cys Cys Thr Pro His
1               5                   10

<210> SEQ ID NO 55
<211> LENGTH: 14
<212> TYPE: PRT
<213> ORGANISM: Mus sp.

<400> SEQUENCE: 55

Cys Asp Phe Gly Ser Pro Ala Asn Arg Lys Ile Gly Val Cys
1               5                   10
```

CCN3 PEPTIDES AND ANALOGS THEREOF FOR THERAPEUTIC USE

CROSS-REFERENCE TO RELATED APPLICATION

This application claims priority to U.S. Provisional Patent Application Ser. No. 61/341,694 filed on Apr. 2, 2010, the entirety of which is incorporated herein by reference and made a part hereof.

FEDERALLY SPONSORED RESEARCH OR DEVELOPMENT

Not Applicable.

SEQUENCE LISTING

The instant application contains a Sequence Listing which has been submitted in ASCII format via EFS-Web and is hereby incorporated by reference in its entirety. Said ASCII copy, created on May 6, 2011, is named 11246195.txt and is 25,154 bytes in size.

BACKGROUND OF THE INVENTION

Field of the Invention

The present invention discloses the role of CCN3 in diseases associated with the overexpression of CCN2, which include but are not limited to fibrosis, wound healing and cancer. More particularly, the present invention discloses CCN3 peptides and analogs designed to the function of full-length CCN3 proteins for use in achieving enhanced anti-fibrotic activity thereby blocking fibrosis and or scar development, and for treating cancer and other disease processes where CCN3 and CCN2 are important. The isolated and purified, or synthesized CCN3 peptides and specific analogs are potentially useful in the prevention and/or treatment of diseases by regulating the expression and/or activity of CCN2, CCN3 and other CCN-related proteins, as well as collagen and other extracellular matrix proteins.

The CCN Family of Genes and Proteins

The CCN family of genes presently consists of six distinct members that encode proteins that participate in fundamental biological processes such as cell proliferation, attachment, migration, embryogenesis, differentiation, wound healing, angiogenesis, and several pathologies, including fibrosis and tumorigensis. Proteins encoded by the members of the CCN gene family are primarily 30-40 kDa proteins and are extremely rich in cysteine (10% by mass) (Perbal B., NOV and the CCN family of genes: structural and functional issues. *Molecular Pathology* 54: 57-79, 2001). More recently, it has been reported that some forms of the CCN proteins (CCN3 included) are in the 35-55 kDa range. They are designated as cysteine-rich 61 (CYR-61) proteins, connective tissue growth factor (CTGF) proteins, nephroblastoma overexpressed (NOV) proteins, Wnt-induced secreted proteins-1 (WISP-1), Wnt-induced secreted proteins-2 (WISP-2), and Wnt-induced secreted proteins-3 (WISP-3). More recently, new nomenclature for this family of genes and proteins has been proposed (see Table 1).

TABLE 1

Proposed Names and Names Currently and Previously Used for CCN Family of Genes and Proteins

| Proposed name | Names used currently or previously |
| --- | --- |
| CCN1 | CYR61 (human, mouse, *xenopus*), CEF10 (chicken), IGFBP-rP4 (human), βIG-M1 (mouse), CTGF-2, IGFBP10 (human), angiopro |
| CCN2 | CTGF (human, mouse, chicken, *xenopus*), βIG-M2 (mouse), FISP12 (mouse), IGFBP-rP2 (human), Hsc24 (human), IGFBP8 (human), HBGF-0.8, ecogenin (human) |
| CCN3 | NOV (human, rat, chicken, mouse, quail), IGFBP-rP3 (human), IGFBP9 (human), NOVH (human), NOVm, mNOV (mouse), xNOV (*xenopus*) |
| CCN4 | WISP-1 (human), ELM-1 |
| CCN5 | WISP-2 (human), CTGF-L, CTGF-3, HICP, rCOP-1 (rat) |
| CCN6 | WISP-3 (human) |

FIG. 1 shows the modular structure of the CCN proteins, in a very simplistic and linear manner. Although they have a quite conserved multinodular organization, with four modules sharing identity with insulin-like growth factor binding proteins (IGFBPs), Von Willebrand factor (VWC), thrombospondin-1 (TSP1), and a cysteine knot (CT) containing family of growth regulators, the CCN proteins have distinctive biological properties, are differentially regulated, and do not have complete, 100% homology with each other when amino acid sequences are compared. Their involvement has been shown in multiple organ systems. One organ that has been the focus of a large number of studies is the kidney. The underlying mechanisms of action of CCN proteins are still incompletely understood. Attempts to identify unique specific high-affinity signal transducing receptors have been difficult. (Brigstock D. R., Regulation of angiogenesis and endothelial cell function by connective tissue growth factor. FEBS Letters 327: 125-130, 2003). However, a number of potential receptors for signaling each perhaps responsible for different activities or functions, have now been tentatively identified (Mason, R., Connective tissue growth factor (CCN2), a pathogenic factor in diabetic nephropathy. What does it do? How does it do it? J. Cell Commun. Signal 3: 95-104, 2009).

CCN2 Gene and its Encoded Protein

Of all the six members of the CCN family, CCN2 has emerged as an important player in its roles in the regulation of certain cellular functions important in skeletal growth and placental angiogenesis, as well as its roles in certain diseases including fibrosis (including renal and diabetes associated fibrosis), vascular sclerosis, atherosclerosis, bone disease, vascular resistance, tumorigenesis and/or cancer cell growth.

CCN2 has been now shown to be a causal factor in renal fibrosis, and appears to act in a similar fashion in other fibrotic diseases, including but not limited to, those occurring in the liver, lungs, heart, skin, vasculature and peritoneum (Dean R. G., Balding L., Candido R., Burns W. C., Cao Z., Twigg S. M., Burrell L, M. Connective tissue growth factor and cardiac fibrosis after myocardial infarction. *Journal of Histochemistry & Cytochemistry.* 53(10):1245-56, 2005; Shi-wen X., Pennington D., Holmes A., Leask A., Bradham D., Beauchamp J. R., Fonseca C., du Bois R. M., Martin G. R., Black C. M., Abraham D. J. Autocrine overexpression of CTGF maintains fibrosis: RDA analysis of fibrosis genes in systemic sclerosis. *Experimental Cell Research.* 259(1):213-24, 2000; Ozaki S., Sato Y., Yasoshima M., Harada K., Nakanuma Y. Diffuse expression of heparan sulfate proteoglycan and connective tissue growth factor in fibrous septa with many mast cells relate to unresolving hepatic fibrosis of congenital hepatic fibrosis. *Liver International.* 25(4):817-28, 2005;

Sakamoto N., Sugimura K., Kawashima H., Tsuchida K., Takemoto Y., Naganuma T., Tatsumi S., Nakatani T. Influence of glucose and inflammatory cytokines on TGF-beta1 and CTGF mRNA expressions in human peritoneal mesothelial cells. *International Journal of Molecular Medicine.* 15(6): 907-11, 2005; Zarrinkalam K. H., Stanley J. M., Gray J., Oliver N., Faull R. J. Connective tissue growth factor and its regulation in the peritoneal cavity of peritoneal dialysis patients. *Kidney International.* 64(1):331-8, 2003.). When expressed in increased amounts, this CCN2 upregulated, for example, by transforming growth factor-β (TGF-β), high glucose concentrations, mechanical stress, advanced glycosylation end products (AGEs), induces (among other things) the over-accumulation of, and sometimes improperly organized, extracellular matrix (ECM) molecules (e.g., collagen forms, and thrombospondin (TSP)). This ECM when organized makes the space separating cells, and includes membranes, connective tissue, and even bone. This abnormal production/accumulation/organization of ECM results in scarring and fibrosis/sclerosis.

Studies with the renal system have provided evidence of the role for CCN2 as an important pathogenic factor in fibrosis/sclerosis in a number of models of chronic kidney disease (CKD). Early reports had suggested a possible interactive role in CCN2 with TGF-β in skin fibrosis and scleroderma (Bradham D M et al, Connective tissue growth factor: a cysteine-rich mitogen secreted by human vascular endothelial cells is related to SCR-induced immediate early gene product CEF-10. *Journal of Cell Biology,* 114:1285-1294, 1991).

The formation of sclerosis or fibrosis in the kidney is a common response to severe or chronic forms of injury. In chronic kidney disease (CKD), there appears to be three predominant causal factors: metabolic, genetic, and hemodynamic. All of these factors can interact, particularly in diabetic nephropathy (DN), to drive progression. CCN2 now appears to be a central, downstream mediator of the effects of these three elements. For example, pathological shear or stretching force resulting from intraglomerular hypertension appears to stimulate the production of cytokines including CCN2. This same force appears to be responsible for increased vascular permeability leading to both proteinuria and an increased production of vasoactive hormones such as angiotensin (AG) II and endothelin, which in turn also elevate CCN2 and further enhance the mechanical force. The abnormal accumulation of advanced glycosylation end products (AGEs) that occur with the altered metabolism of glucose in DN may also work to both directly increase extracellular matrix (ECM) cross-linking and accumulation, as well as to increase CCN2. The genetic background of the individual can influence the elements of hemodynamics and metabolism and in turn the resulting pathways as described. Additionally, there is a likely influence of genetics on protein kinase C (PKC) activity and production of vasoactive hormones. In all cases, the chronic upregulation of CCN2 activity is likely to result in altered ECM turnover and increasing ECM accumulation, producing fibrosis or sclerosis (In: Contemporary Diabetes: *The Diabetic Kidney*, C E Mogensen & P. Cortes (eds), Humana Academic Publishers, Totowa, N.J., June 2006, Riser, B L et al. CCN2 (CTGF) in the pathogenesis of diabetic renal disease: A target for therapeutic intervention). These findings support the postulate that CCN2 is a central downstream element in the progression of fibrosis, and as such provides a reasonable and novel target for both diagnostics and therapeutic purposes. Additional support for this in renal fibrosis has come from data in humans showing that the level of renal CCN2, and/or that passing into the urine can be measured and used to predict the onset of renal disease and/or fibrosis as well as to stage progression. This has been supported by a number of reports showing that the level of CCN2 present in the kidney glomerulus, or even passing into the urine predicts the future onset, and stages renal disease (including fibrosis) (*Kidney International, 64*:451-458, 2003. Riser, B L et al, CCN2 (CTGF): as a possible predictor of diabetic nephropathy: Preliminary report, *Cytokine,* 47, 1:37-42 2009, F K Tam, et al, Urinary monocyte chemoattractant protein-1 (MCP-1) and connective tissue growth factor (CCN2) as prognostic markers for progression of diabetic nephropathy)

CCN2 is estrogen inducible and overexpressed in steroid-dependent breast or uterine tumors (Tsai et al., Expression and function of CYR61, an angiogenic factor, in breast cancer cell lines and tumor biopsies. *Cancer Research* 60: 5602-5607, 2000; Tsai et al., Expression and regulation of Cyr61 in human breast cancer cell lines. *Oncogene* 21: 964-974, 2000; Sampath et al. Cyr61, a member of the CCN family, is required for MCF-7 cell proliferation: regulation by 17 beta-estradiol and overexpression in human breast cancer. *Endocrinology* 142: 2540-2548, 2001; Sampath et al., Aberrant expression of Cyr 61, a member of the CCN family (i.e. CCN1), and dysregulation by 17 beta-estradiol and basic fibroblast growth factor in human uterine leiomyomas. *Journal of Clinical Endocrinology and Metabolism,* 86: 1707-1715, 2001; Sampath et al, The angiogenic factor Cyr61 is induced by progestin R5020 and is necessary for mammary adenocarcinorma cell growth. *Endocrine,* 18: 147-150, 2002; Xie et al., Breast cancer, Cyr61 is overexpressed, estrogen-inducible, and associated with more advanced disease. *Journal of Biological Chemistry,* 276: 14187-14194, 2001; Xie et al., Elevated levels of connective tissue growth factor, WISP-1, and CYR61 in primary breast cancers associated with more advanced features. *Cancer Research,* 61: 8917-8923, 2002). CCN2 and other CCN family members are important downstream mediators of estrogen- and progesterone-regulated cell growth. CCN2 and other CCN proteins may also impact other growth regulatory pathways in breast cancer cells. Uterine CCN2 is regulated by both estrogen and progesterone and appears to be important for maintenance or remodeling of stromal ECM (Rageh et al., Steroidal regulation of connective tissue growth factor (CCN2; CTGF) synthesis in the mouse uterus. *Molecular Pathology,* 56: 80-85, 2001; Cheon et al., A genomic approach to identify novel progesterone receptor regulated pathways in the uterus during implantation. *Molecular Endocrinology,* 16: 2853-2871, 2002). In the ovary, CCN2 is regulated by gonadotropins or transforming growth factor-beta (TGF-β) and is associated with thecal cell recruitment and mitosis, and maintenance of the corpus luteum (Wandji et al., Messenger ribonucleic acids for MAC25 and connective tissue growth factor (CTGF) are inversely regulated during folliculogenesis and early luteogenesis. Kidney International, 60: 96-105, 2000; Slee et al., Differentiation-dependent expression of connective tissue growth factor and lysyl oxidase messenger ribonucleic acids in rat granulose cells. *Endocrinology,* 142: 1082-1089, 2001; Harlow & Hillar, Connective tissue growth factor in the ovarian paracrine system. Molecular and Cellular Endocrinology, 187: 23-27, 2002; Harlow et al., FSH and TGF-beta superfamily members regulate granulose cell connective tissue growth factor gene expression in vitro and in vivo. *Endocrinology,* 143: 3316-3325, 2002; Liu et al., Gonodotrophins inhibit the expression of insulin-like growth binding protein-related protein-2 mRNA in cultured human granulose-luteal cells. *Molecular Human Reproduction,* 8: 136-141; 2002).

U.S. Pat. No. 7,780,949 by Riser and DeNichilo discloses the role of CCN2 in the production of extracellular matrix (ECM), as well as methods for diagnosing the presence and progress of pathologies characterized by an accumulation of the ECM components by measuring the level of CCN2 in a sample. The method is directed to diagnosing kidney fibrosis and associated renal disorders, in particular, complications associated with diabetes, hyperglycemia and hypertension.

CCN3 Gene and its Encoded Proteins

CCN3 is another member of the CCN family. It has been reported that CCN3 exists in various forms. In a study to construct retroviral competent ovian recombinants, it has been demonstrated that the CCN3 protein can be expressed either as a full-length protein with a molecular weight of about 50 kDa or a smaller truncated protein, which is a fragment of the full length protein (Perbal B., *J. Clin. Pathol: Mol Pathol.* 54: 57-79, 2001). Other forms of CCN3 protein have also been reported. For example, a CCN3 related protein has been detected at the nuclear envelope of the NCI-H295R cells and another CCN3 related protein binds the promoter of human plasminogen activator inhibitor type 2 (PAI-2) (Perbal B., *J. Clin. Pathol: Mol Pathol,* 54: 57-79, 2001). K19M-AF antibody directed against C-terminal 19-aminoacid peptide of CCN3 revealed at least two conformational states of the native CCN3 protein (Kyurkchiev S. et al., Potential cellular conformations of the CCN3 (NOV) protein. *Cellular Communication and Signaling,* 2: 9-18, 2004). Cytoplasmic and cell membrane bound CCN3 has an exposed C-terminus while secreted CCN3 has a sequestered C-terminus which could be due to interaction with other proteins or itself (dimerization).

The amino acid sequences of the full length CCN3 proteins from various species, including human, have been fully characterized and are disclosed by Li et al. (Li, C. L. et al., A role for CCN3 (NOV) in calcium signaling. *Journal of Clinical Pathology: Molecular Pathology,* 55: 250-261, 2002). One CCN3 full length protein has about 357 amino acids.

U.S. Pat. No. 7,780,949 by Riser discloses that the full-length CCN3 molecule blocks fibrosis in an in vitro model of renal fibrosis by acting, at least partially, through its ability to down-regulate the profibrotic activity of CCN2. CCN3 was not previously known to have activity in fibrosis or wound healing/scarring, either as a positive or negative factor and was not known to have a regulatory effect on CCN2. U.S. Pat. No. 7,780,949 shows that the full-length CCN3 proteins can work to inhibit the production and actions of CCN2, and thus the overproduction of extracellular matrix that characterizes fibrosis in many organs. Neither the above patent application, nor other patent or published literature, disclose whether a smaller portion of the whole CCN3, or a peptide, is capable of ing this activity. It is now understood that fibrosis, although initiated by a variety of different insults, once started follows a common pathway apparently always involving one, or both of TGF-beta and CCN2 as causal factors. Therefore, having shown that CCN3 can be used to prevent and or treat fibrosis and abnormal production/accumulation of ECM .e.g. collagen in renal cells and renal disease, one can reasonably assume that it will be useful in such disease in other organs, and even those initiated by different stimuli or insults. U.S. Pat. No. 7,780,949 further discloses measuring CCN3 levels for diagnosis and prognosis of renal disease.

The present invention is directed to isolating newly described, newly produced, specific, effective CCN3 derived peptides, as a substitute for the full-length CCN3 protein, to achieve equal or better anti-CCN2 and anti-fibrotic activity, also producing novel manufacturing and delivery advantages. In a preferred form of the invention, it was surprisingly found that a small number of peptides having fourteen amino acids (CCNp37, CCNp38 (human and mouse) and cysteine-substituted versions of these peptides) were effective in treating pathologies associated with the over-accumulation, disregulation of turnover, or altered composition, of extra-cellular matrix proteins. These short peptides are far smaller than the full-length CCN3 protein and are likely to be more easily synthesized and formulated for delivery to a patient in need thereof. These and other aspects and attributes of the present invention will be discussed with reference to the following drawings and accompanying specification.

BRIEF DESCRIPTION OF THE DRAWINGS

FIG. 2 shows a published mouse sequence of CCN3 (SEQ ID NO: 41) used for design of peptides (upper sequence), and our modified sequence (SEQ ID NO: 42) with the replacement of cysteines with serines, which does not exist in nature (lower sequence);

FIG. 3 shows specific CCN3 sequences (peptides 1-40 disclosed as SEQ ID NOS 1-40) then used to generate small peptides that were tested for activity;

FIG. 4 shows the overall structure and sequence alignment of human CCN (hCCN), showing both hCCN2 (SEQ ID NO: 43) and hCCN3 (SEQ ID NO: 44) as the computer aligned them, with a schematic diagram of the four described modules shown in the upper part of the figure, including IGF-BD, VWF, TSP and the c-terminal repeat element. The lower portion of the figure shows the sequence alignment (marked by asterisks) of the two molecules (hCCN2 and hCCN3) here with the cysteines intact;

FIG. 6 shows the CCN3 sequences chosen for peptide design which were targeted based on their position in the molecule and sequence homology with CCN2. Ultimately, the cysteines were replaced with serine to avoid potential formation of circular structures produced by the charge of the cysteine and thus the obliteration the normal, or targeted function we were seeking. However, we also did not know if this change would result in complete loss of the functions sought. These peptides were at the same time chosen also for their high homology between human and murine, so that any sequence tested in and proven effective in murine models would be expected to provide a same level of efficacy in humans. FIG. 6 discloses SEQ ID NOS 45-49, respectively, in order of appearance.

FIG. 7A shows the specific CCN3p37 (SEQ ID NO: 37) and CCN3p38 (SEQ ID NO: 38) peptides that were synthesized and tested having the cysteine residues replaced by serine residues.

FIG. 7B is a comparison showing the degree of homology between murine and human natural sequences from which CCN3p37 and CCN3p38 were derived. CCNp37 is identical between human (SEQ ID NO: 50) and mouse (SEQ ID NO: 48). Peptide CCN3p38 has only one amino acid difference between human (SEQ ID NO: 51) and mouse (SEQ ID NO:

49). A cysteine-substituted human CCN3p38 (SEQ ID NO 56) would have a sequence of SDRSADPSNQTGIS.

FIG. 7C shows a comparison of naturally occurring human CCN2 and CCN3 sequences at regions selected for CCN3p37 and CCN3p38. For CCNp37 sequence chosen, both CCN2 and CCN3 have an unsual high homology over these sequences at regions, with only one amino acid difference out of fourteen. In great contrast, for the CCN3p38 sequence chosen, CCN2 and CCN3 have an unusually low amino acid homology with only four alike out of fourteen aminoacids. FIG. 7C discloses SEQ ID NOS 52, 50, 53, and 51, respectively, in order of appearance.

FIG. 7D shows a comparison of naturally occurring murine CCN2 and CCN3 sequences at regions CCN3p37 and CCN3p38. For CCN3p37 there is no difference from what was shown in 7C above, since they are no difference between human and mouse. For CCN3p38, there are 4 of 14 amino acids that match the sequence of CCN2 in the naturally occurring sequences. FIG. 7D discloses SEQ ID NOS 54, 48, 55, and 49, respectively, in order of appearance.

Figure 8:
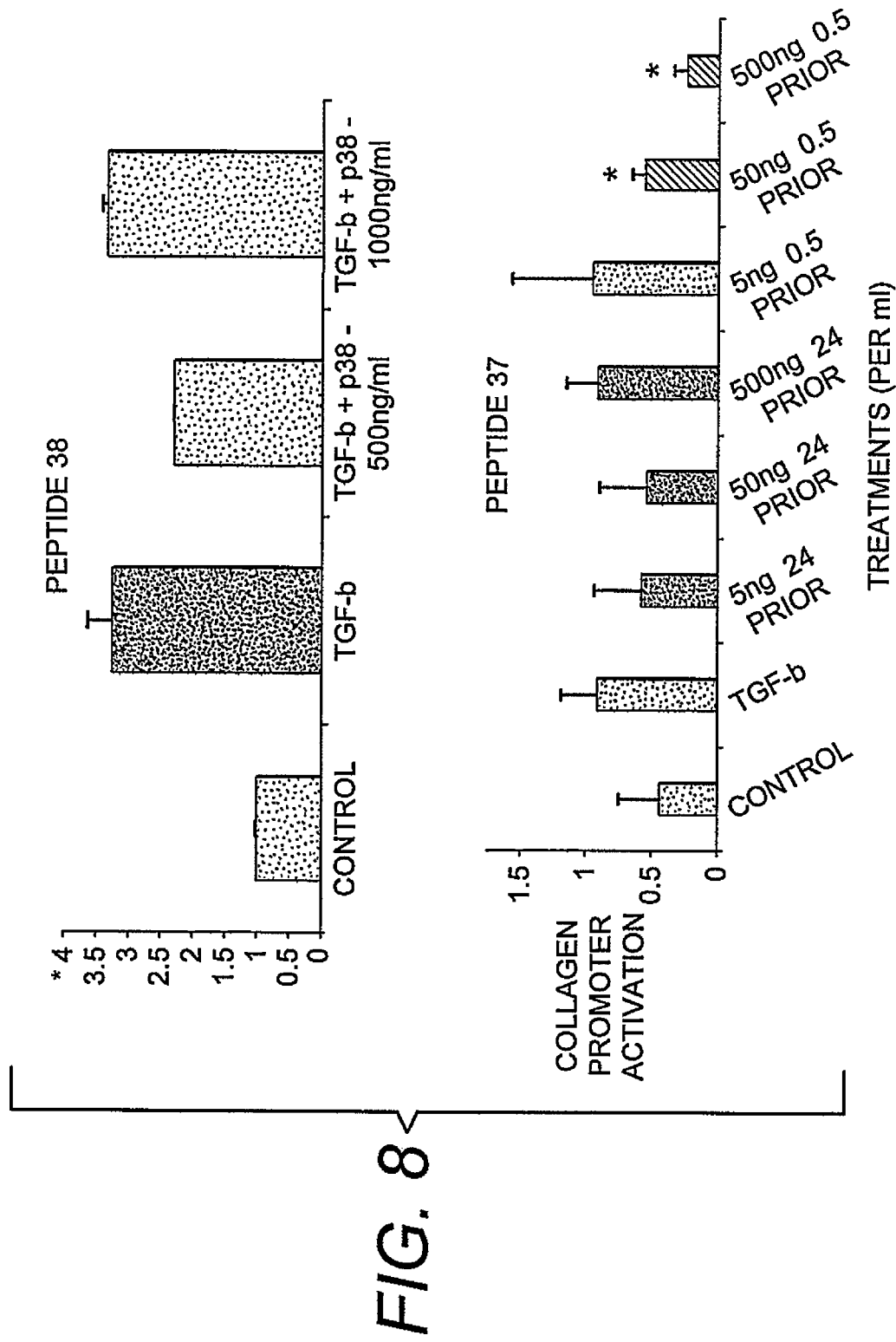

FIG. 8 shows that CCN3p37 and CCN3p38 reduce collagen promoter stimulation by TGF-β. Peptide 38 (TOP) was able to inhibit collagen promoter activity at 500 ng/mL. Peptide 37 demonstrated an ability to totally block TGF-β-stimulated collagen promoter activity when added just prior to TGF-β (right 3 bars in lower figure). This inhibitory activity was also present (although to a lower level) even when added 24-hours prior to TGF-β. None of the other 38 peptides made and tested showed activity in this assay, so the data are not shown. The Y-axis in the top figure is the level of collagen promoter activation (in arbitrary units), based on a transfection efficiency control (CMV promoter activation), as also shown in the lower figure.

Figure 9:
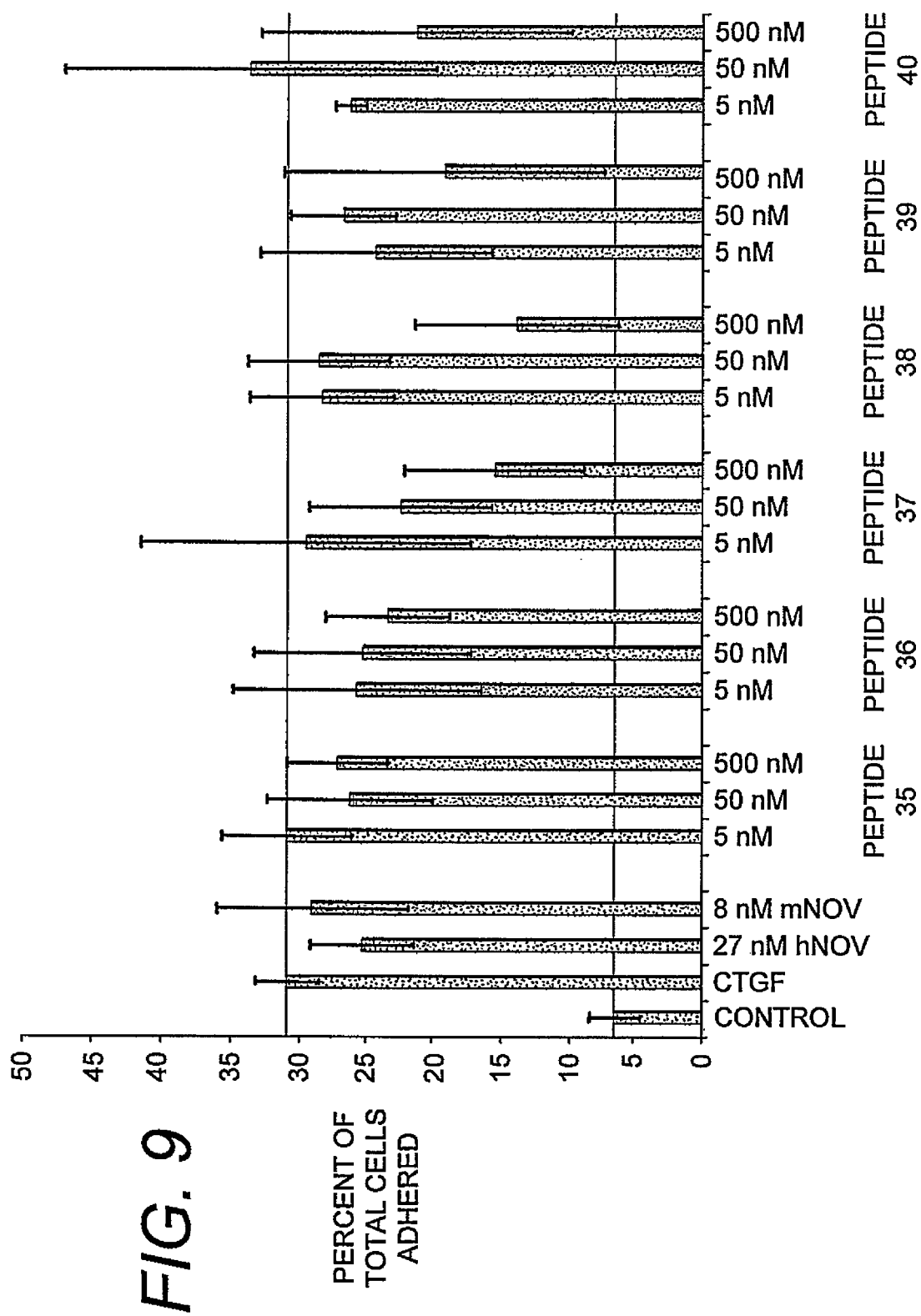

FIG. 9 shows CCN3p37 and CCN3p38 dose-dependently blocking the cellular adhesion to CCN2 coated plates. Control plates show the adhesion of mesangial cells to plastic only (uncoated) plates. "CTGF" or CCN2, the second bar from the left, shows the marked increased adhesion mediated by receptor binding to CCN2-coated plates, as opposed to that occurring on the uncoated plastic. Full-length CCN3 (NOV) human (27 nM) added just prior to the treatment with TGF-β, provided some inhibition of this binding as expected. However, peptides CCNp37 and CCNp38 dose-dependently blocked the receptor binding mediated to CCN2, providing approximately 60% to 70% inhibition at the highest concentration tested (500 nM). This indicates that the two peptides are able to interact at the binding site. None of the other 38 peptides tested (only p35, p36, p37 and p40 of those shown here for space considerations) were able to significantly block binding. The specific activity shown for peptides CCNp37 and CCNp38 in this assay demonstrate an ability to block the receptors on the cells that would bind CCN2, and would be required for certain specific activities.

FIG. 10A shows CCN2 immunolocalization (reactivity with protein specific antibody) and the inhibitory effect of peptide CCN3p37. Here shown, TGF-β treatment results in a dramatic loss (secretion) of the already made CCN2 localized at the cell membrane (dark reddish brown) but also initiates the synthesis new CCN2, now seen in the cytoplasm (light reddish brown. Along with this, is a phenotype change to a more elongated angular, fibroblast-type cell, characteristic of that seen in fibrosis. Treatment with CCN3p37 at 50 nM blocks this phenotypic transition, and reduces greatly the expulsion of CCN2 and new synthesis of new CCN2.

Figure 10B:
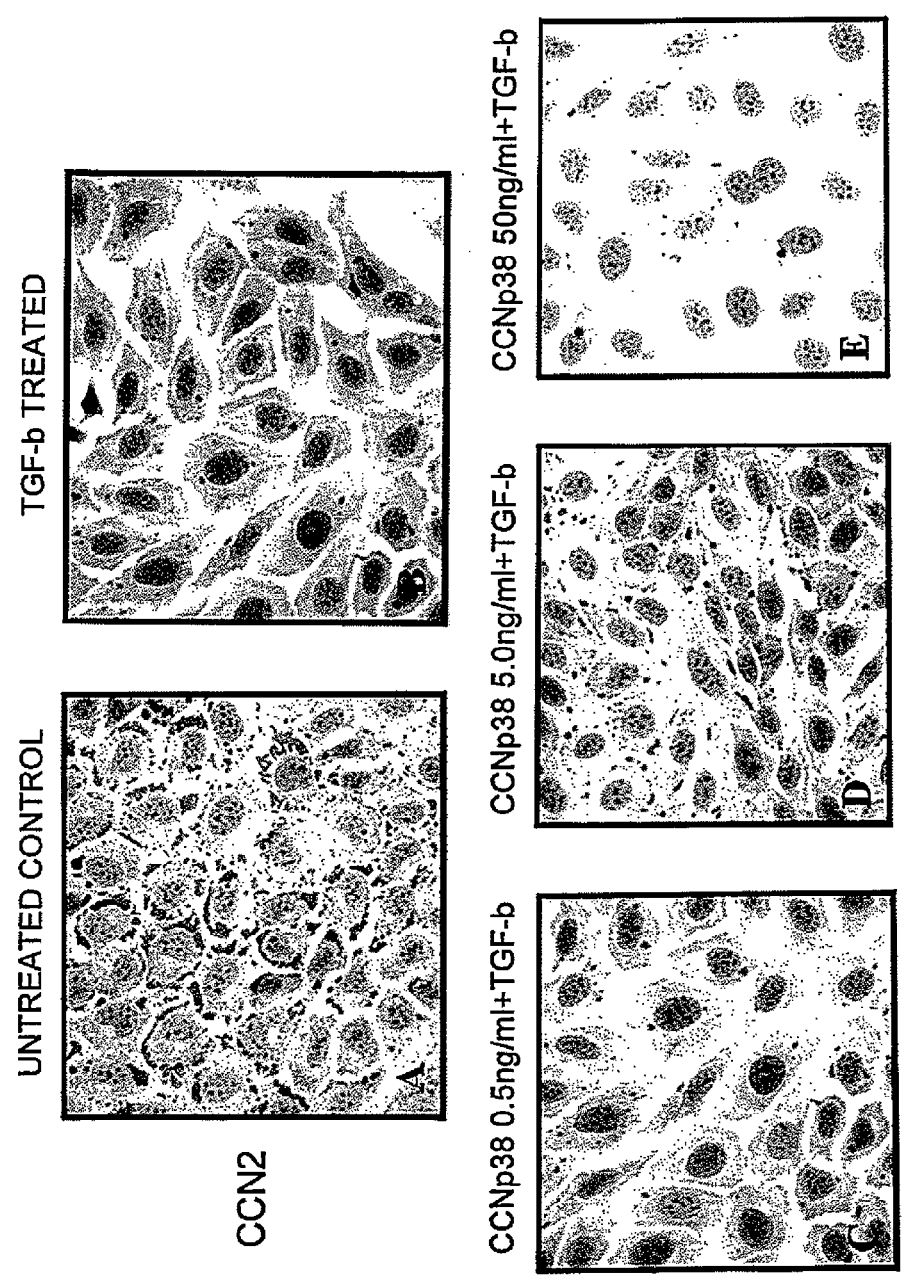

FIG. 10B shows CCN2 immunolocalization and the inhibitory effect of peptide CCNp38. The untreated control cells show extensive CCN2 (brown) at the cell borders. TGF-β treatment results in a dramatic loss (secretion) of CCN2 at the cell membrane and the initiation of new synthesis now seen throughout the cytoplasm. Along with this is a phenotype change to what appears to be a fibro-blast type cells, characteristic of fibrosis. Treatment with CCN3p38 blocks this phenotypic transition, the expulsion of CCN2, and new synthesis of CCN2. The optimal effect appears to be at 50 nM, with a dose response effect occurring with lower concentration. Other peptides did not produce this effect (not shown).

FIG. 11A shows collagen I immunolocalization and the inhibitory effect of peptide CCNp37. TGF-β (a potent stimulator of collagen accumulation and fibrosis) treatment results in a dramatic loss or secretion of the abundant collagen I at the cell membrane (shown in the control frame as brown or reddish brown) and the initiation of some new synthesis seen throughout the cytoplasm (TGF treated). Along with this is a phenotype change to what appears to be an elongate, less cuboidal, fibroblast-type cell characteristic of fibrosis. Treatment with CCNp37 at a low concentration of 0.5 nM blocks this phenotypic transition, the expulsion of CCN2 and new synthesis of CCN2. Higher doses show the same or similar effect. Other peptides did not show this effect (not shown).

Figure 11B:
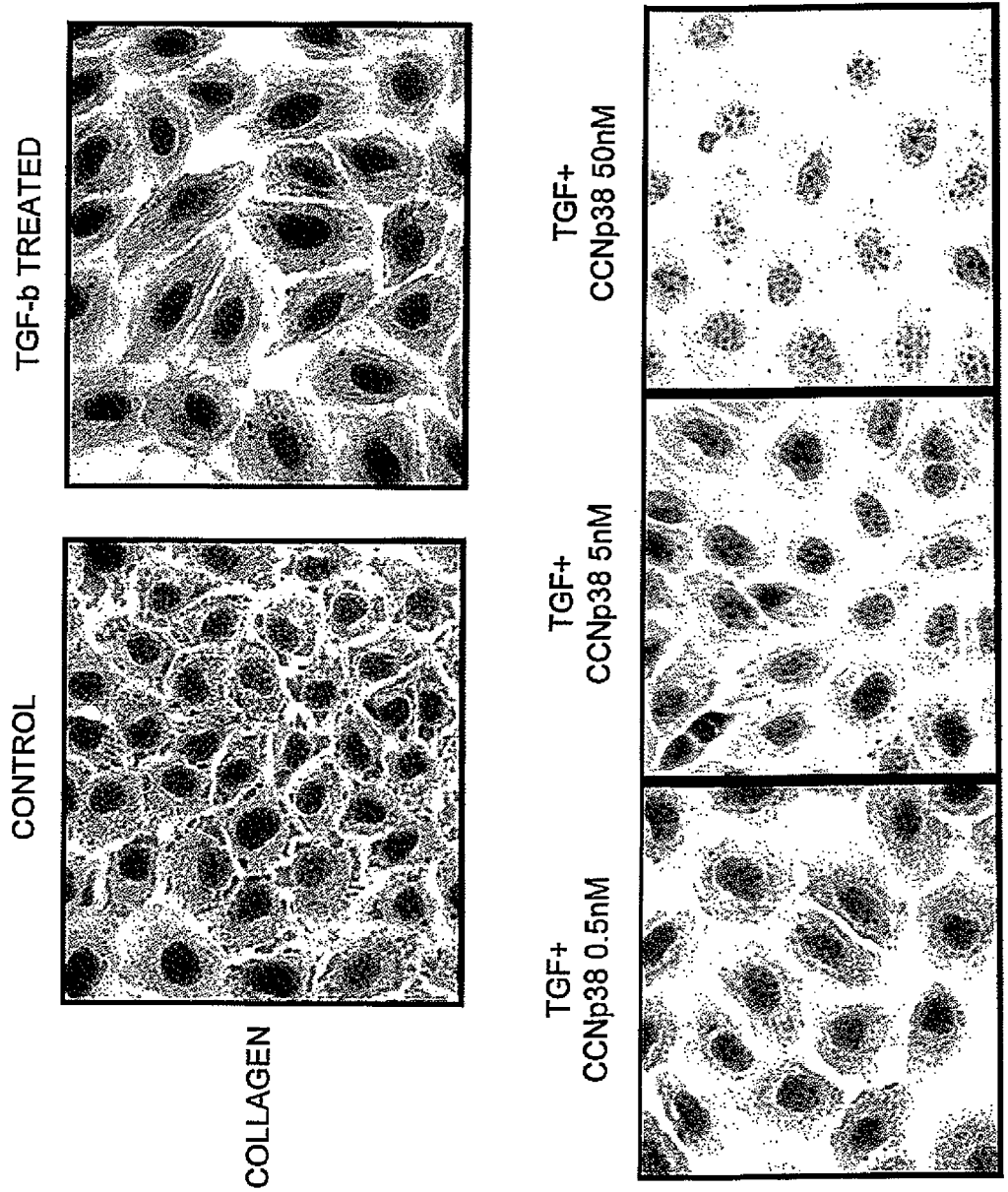

FIG. 11B shows collagen I immunolocalization and the inhibitory effect of peptide CCNp38. Treatment with TGF-β (a known pro-fibrotic agent) results in a dramatic loss (secretion) of the abundant collagen I at the cell membrane (shown in the control frame) and the initiation of some new synthesis seen throughout the cytoplasm (TGF treated). Along with this is a phenotype change to what appears to be an elongate, less cuboidal, fibro-blast type cell. Treatment with CCN3p38 at low concentration of 0.5 nM has little effect. However, at doses of 5-50 nM there is a blockade the phenotypic transition, the expulsion of some of the premade collagen and new synthesis of collagen that occurs in response to TGF-β. Other peptides did not demonstrate this effect (not shown).

Figure 12:
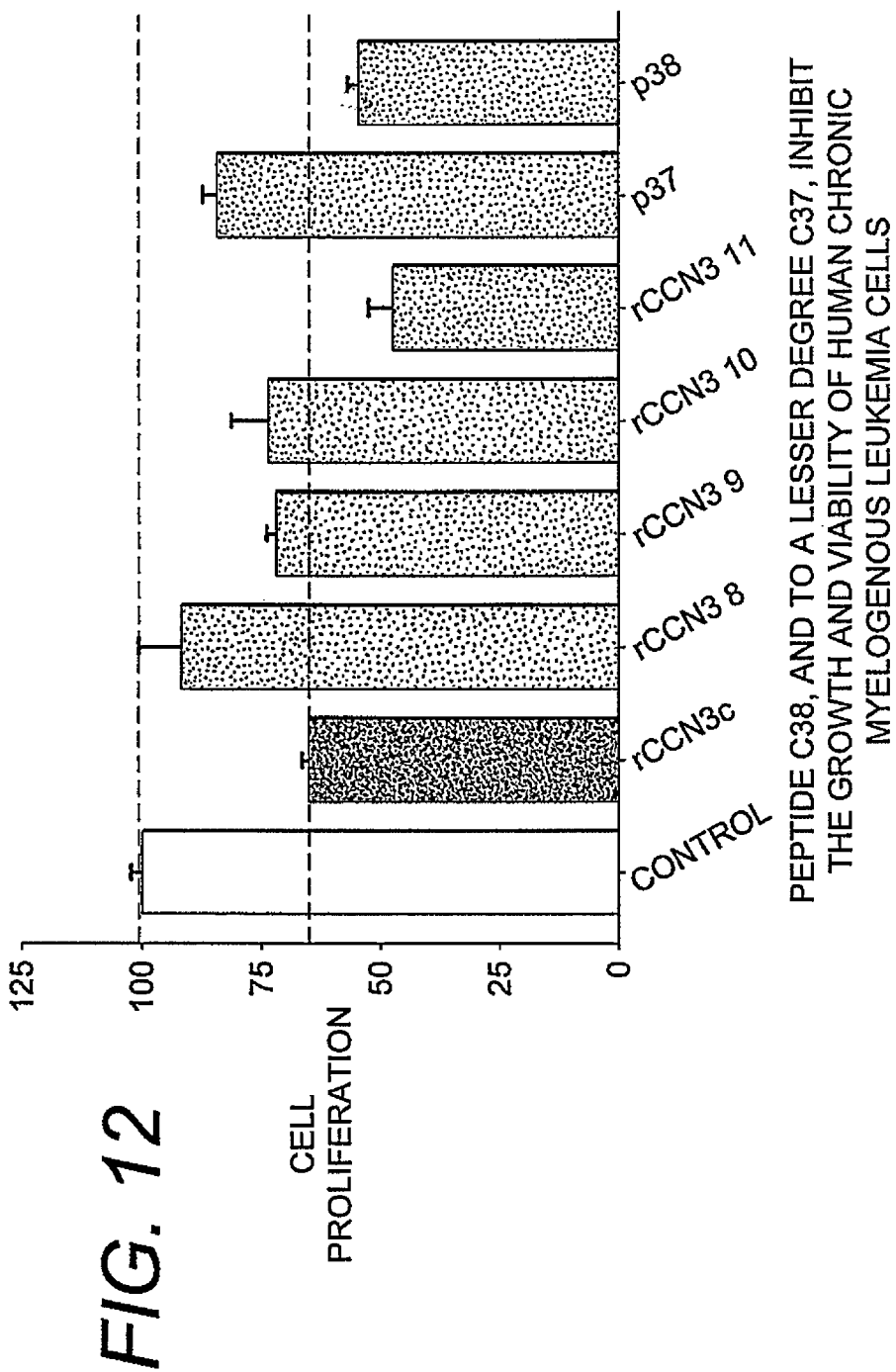

FIG. 12 shows a bar graph of cell proliferation of human chronic myelogenous leukemia in untreated cells (Control) and compared to those pre-incubated with quantities of a commercial recombinant CCN3 (rCCN3c), full length CCN3 protein made in our laboratory rCCN3 8, rCCN3 9, rCCN3 10, rCCN3 11, or CCN3p37 or CCN3p38. CML cells were allowed to grow, then proliferation measured by the CellTiter-Glo®Luminescent Cell Viability Assay Control untreated cells, or cells. The latter is a homogeneous method of determining the number of viable cells in culture based on quantitation of the ATP present, an indicator of metabolically active cells. The commercially produced full length CCN3 produces an approximate 35% reduction in growth and/or viability over the period tested. CCN3p37 produces 15-20% inhibition and CCNp38 approximately 40% inhibition.

DETAILED DESCRIPTION OF THE INVENTION

While this invention is susceptible of embodiments in many different forms, there is shown in the figures, and will be described herein in detail, specific embodiments thereof with the understanding that the present disclosure is to be considered as an exemplification of the principles of the invention and is not intended to limit the invention to the specific embodiments illustrated.

Selection of the CCN3 Peptides

The present invention discloses a role of CCN3 derived peptides in diseases associated with the over-accumulation, disregulation of turnover, or altered composition of extracellular matrix molecules in a human subject, which can lead to fibrosis, wound healing and cancer cell/tumor growth. Certain CCN3 peptides of the present invention can be used as a substitute for full-length CCN3 protein, to achieve equal or greater anti-fibrotic activity. The term "fibrosis" used in the present disclosure is used interchangeably with the term "sclerosis" and scar formation since they are similar processes involved in the overgrowth of fibrous or fibrosis-like tissue and for the increased, abnormal deposition and/or assembly/organization of extracellular matrix molecules such as collagen, and all have been shown to have CCN2 as at least a causal factor.

In order to isolate the CCN3 peptides, a series of 36 short overlapping peptide sequences, beginning at, and defined by, the n-terminal region and working to the c-terminal end of the CCN3 were generated. Short overlapping sequences are defined herein as sequences ranging in size from about 10 to 18 amino acids and more preferably 12 to 17 amino acids even more preferably 13-15 amino acids and most preferably 14 amino acids (or any range or combination of ranges therein) and overlap each other on the full-length protein sequence by about 3 to 7 amino acids. Murine models of fibrosis were used to verify fibrotic activity, therefore murine CCN3 sequences were used. It is well-known in the art that human CCN3 has a strong homology with murine. In fact, the mouse and the human sequences for the region chosen for peptide CCN3p37 are identical, whereas for CCN3p38 there is only a single amino acid difference between the human and the mouse. FIG. 2 shows the published mouse CCN3 sequence and the location of cysteine residues that were replaced by serine residues, in order potentially to aid in the prevention of circularization of the peptides, and loss of activity. On the negative side, this substitution could also have the potential to eliminate all biological activity ascribed to CCN3, especially since it is known to be a "cysteine-rich molecule" and its know function could therefore be dependent on the presence of cysteines. The effect of this change could not be predicted before our work. The serine modified peptide sequences shall sometimes be referred to as analogs or serine analogs of CCN3 peptide sequences. FIG. 3 shows the sequence of the overlapping peptides that were synthesized and tested (peptides 1-35).

Figure 1:
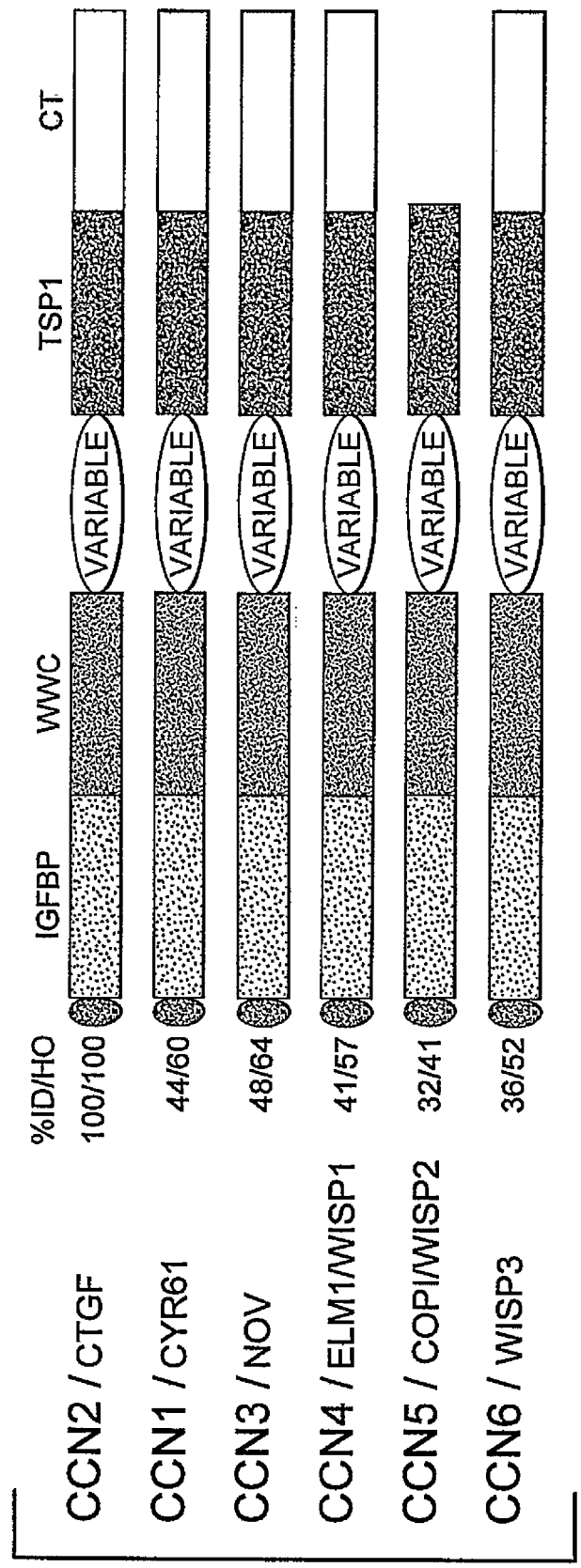
FIG. 1 shows in a very simplistic manner, the general multimodular structure of the CCN proteins. CT, cysteine knot containing family of growth regulators-like domain; IGFBP, insulin-like growth factor binding protein-like domain; TSP1, thrombospondin-like domain; and VWC, Von Willebrand factor-like domain.
Figure 5:
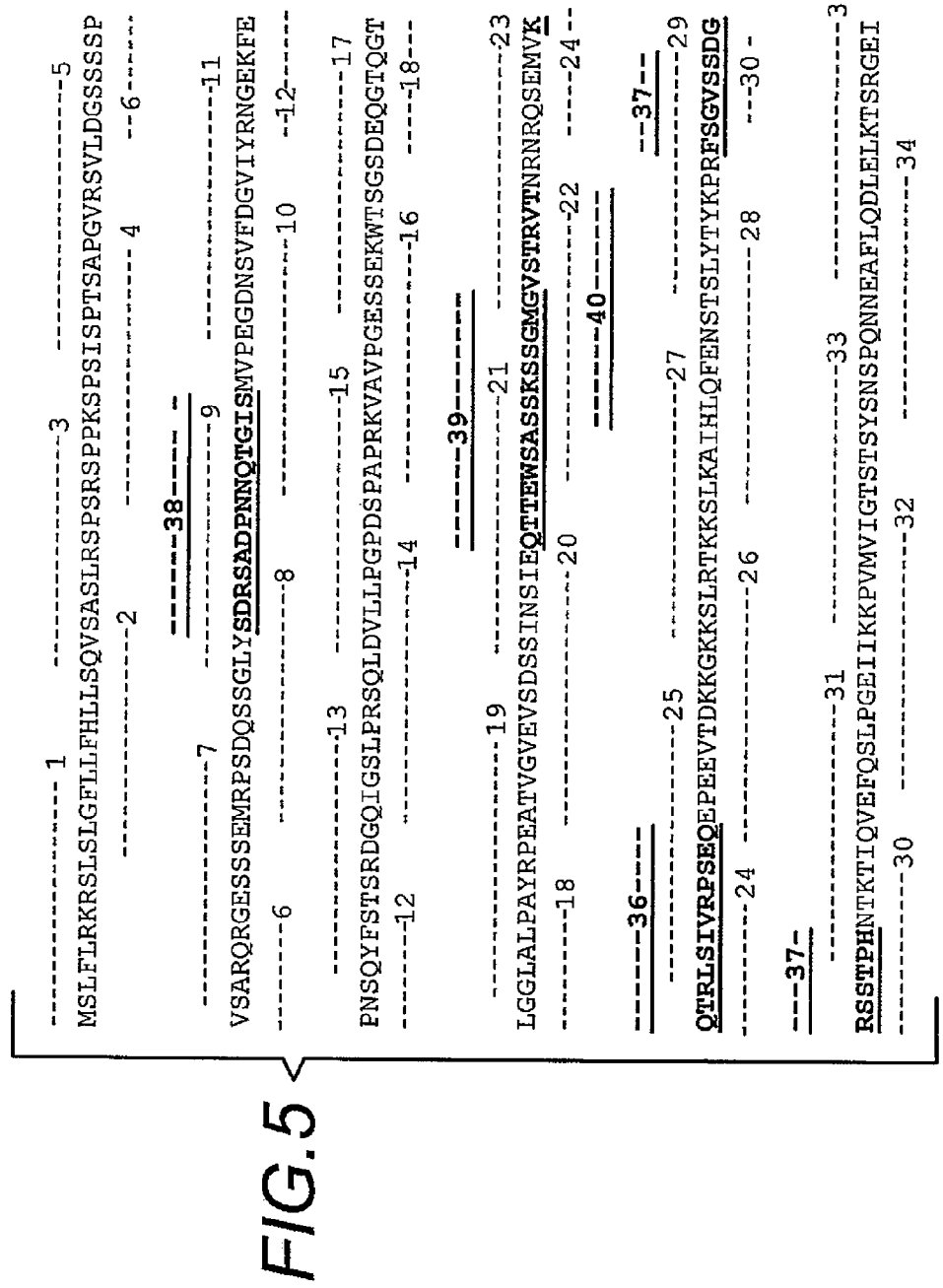
FIG. 5 shows the position of the synthesized CCN peptides (CCNp) on mouse CCN3 (SEQ ID NO: 42) sequence showing the 35 constructed overlapping sequences (CCNp1-35) beginning at the n-terminal end and running to the c-terminal end in black as well as the 5 specifically designed peptides CCNp 36-40 bolded (all here also with the cysteines replaced with serines)

Since CCN2 and CCN3 are members of the same family, but possess different apparent biological functions (in the case of effect on collagen it was found opposite activities), this suggested to us that at least one mechanism for the observed blocking activity of CCN2 (and later collagen production) might be due to receptor competition. That is, CCN3 might interact with a CCN2 receptor preventing CCN2-mediated signaling. CCN3 might possess a sequence that is recognized by the CCN2 receptor, but when bound would not allow signaling for increase matrix production or accumulation, i.e., it could act as a natural, competitive. This was not obvious however, because we also found that CCN3 also greatly inhibited CCN2 synthesis, so it remained possible that the activity was not due to a receptor blockade, but instead due to an inhibition in the production of CCN2. Nevertheless, the two proteins, CCN3 and CCN2, were examined for similarities and differences in amino acid sequence (structure), after producing a computer-generated "best-fit" alignment as shown in FIG. 4 starting with the human sequence. For the reasons hypothesized above, four regions with very high complementary in amino acid sequences (ie., between CCN2 and CCN3) were chosen from both the TSP-like element (referred to as CCN3p39, CCN3p40, and CCN3p36) and the C-terminal module (referred to as CCN3p37) (FIGS. 4 and 5). Also selected was one region within the insulin-like growth-factor binding domain of CCN3, referred to as CCNp38, where it was observed that CCN3 and CCN2 had unusually low (10%) complementary over a relatively large region (shown in FIGS. 4 and 5). It was possible that this unique difference discovered might be responsible for the different actions of CCN2 versus CCN3. All of the peptide sequences, namely CCN3p39, CCN3p40, CCN3p36, CCN3p 37 and CCN3p38, were further reduced by replacing any cysteine residues with serine residues. Consequently, such serine modified peptide sequences are analogs of the CCN3 peptide sequences and could possibility possess similar anti-fibrotic activity as we observed with the full-length protein. It is also contemplated that the cysteine residues could also be replaced by alanine, glycine, S-methylated cysteine or combinations thereof (including serine).

The present invention contemplates that the CCN3 peptide sequences and their analogs discovered have the same, similar, or greater CCN2 inhibitory activity as the full length protein. As discussed in further detail below, we were surprised to find that two short peptides, CCN3p37 and CCN3p38, demonstrated significant CCN2 inhibitory activity while the 38 other peptides screened were not effective in inhibiting CCN2 expression. Thus, these peptides are useful in the treatment of pathologies associated with the over-accumulation, disregulation of turnover, or altered composition of extracellular matrix molecules in the subject.

FIG. 6 shows the sequences chosen for the 4 specifically designed and made peptides (36-40) and states the approximate homology to the best matching of the CCN2 sequence. Three were chosen for their high homology (p37, 39, 40) to CCN2 sequences, one for its low homology (p38), and one for its average (50%) homology (p36). More particularly, FIG. 7A shows peptide sequences CCN3p37 and CCN3p38 that were selected and synthesized by replacing the cysteine residues with serine to possibly prevent circularization of the molecule and loss of activity. As discussed above, murine peptides were selected for testing because of its high degree of homology with humans which is illustrated in FIG. 7B, and the use of murine models to demonstrate efficacy, predicting the human response. Finally, FIG. 7C and FIG. 7D demonstrate that while a strong homology exists between CCN2 and CCN3 at the peptide sequence of CCNp37, that same homology does not exist at peptide sequence CCNp38.

Results from the Screening of Selected CCN3 Peptides

The peptides selected above, and shown in FIG. 5, were synthesized and tested in the three different in vitro assays constructed to model fibrosis, or fibrosis-related pathology in vivo for anti-fibrotic activity. These assays have been used extensively by us and others, and are highly predictive of related responses in vivo, including those occurring in humans. One in vitro assay, ie., of cell adhesion in vitro was used. There is a requirement for adhesion in wound healing and fibrosis, with cells responding to the binding of CCN2 to their receptors for other critical activities. Also alteration of cell attachment and receptor binding is implicated in other non-fibrotic diseases, previously named in this application. For this adhesion assay, a well of a culture plate was coated with CCN2 protein and then rat mesangial cells were added for a defined period. Since the mesangial cells possess CCN2 receptors, they bind tightly to the plate via the specific receptor and therefore adhesion via this receptor can be measured. After a standard period of incubation, the cells are washed to remove non-attached cells. These adherant cells are then removed and counted to determine the percent of the total cells that adhered. The ability of each peptide to block this binding was examined by preincubating cells with the peptide of interest. Controls were used for comparison without CCN2 coating. In a second assay, the ability of the peptide to block the stimulation of collagen type I promoter by TGF-beta was tested. Collagen type I upregulation is a characteristic feature of fibrosis and is often used as an end point determination. TGF-beta is a well-established pro-fibrotic factor or cytokine that mesangial cells and other cells in the fibrotic response respond to by upregulating collagen and other matrix molecule production and accumulation. Several new anti-fibrotic therapies are under development that target the activity of TGF-beta. For the assays used in connection with the present invention, collagen promoter activity was measured as a rapid and early indicator of collagen-related fibrotic activity. The cells in culture were either unstimulated or stimulated by TGF-beta, both in the presence and absence of the selected peptides. If the peptides have inhibitory activity, the promoter activity under TGF-beta stimulation would be reduced to some value approaching the control, non-TGF-beta treated cells. The collagen promoter assay is based on the transfection of mesangial cells with a COL 1a2 promoter linked to luciferase. Therefore, when the promoter is stimulated it can be measured as luciferase units (Riser et al, CCN3 is a negative regulator of CCN2 and a novel endogenous inhibitor of the fibrotic pathway in an in vitro model of renal disease, American J Pathology, 174, 5, 2009). The level of collagen promoter activation (in arbitrary units), is based on a transfection efficiency control (CMV promoter activation), as also shown in the lower figure.

In a third assay, and immunochemical staining was developed that allowed for measuring cellular changes in response to TGF-beta stimulation in both the amount and distribution of CCN2 as well as collagen type I (a prototypical ECM molecule altered in fibrosis, atherosclerosis, vascular calcification, bone disease, and other related disease). This assay also allows one to determine if there is a phenotype change of the cells, particularly to a more fibroblastic-like cell. This change is characteristic in fibrosis, not only in mesangial cell in renal fibrosis but also other cell types can cause fibrosis. This assay is therefore applicable to test the effect of synthesized peptides (Riser et al, CCN3 is a negative regulator of CCN2 and a novel endogenous inhibitor of the fibrotic pathway in an in vitro model of renal disease, American J Pathology, 174, 5, 2009).

The results from the peptide screens showed no significant inhibition of CCN2-mediated binding or of collagen promoter-inhibitory activity for any of the 36 overlapping peptides in either the collagen promoter or the CCN2-mediated adhesion assay. For peptide 37 (CCN3p37) designed to a specific region in the c-terminal module with high (nearly 100%) complementary, both inhibition of TGF-beta stimulated collagen promoter activity (FIG. 8) was found, as well as inhibition of receptor binding (adhesion to CCN2) (FIG. 9). CCN3p37 appeared to be more potent than CCN3p38 in inhibiting collagen promoter activity, and treatment immediately prior to TGF-beta was most effective, however, even a 24 hour prior exposure was able to produce some activity. CCN3p37 and p38 had similar effectiveness in inhibiting TGF-beta stimulated adhesion to CCN2. None of the other overlapping peptides or those specifically designed peptides showed any consistent inhibitory activity. Some peptides were even observed to enhance the promoter activity. CCN3p38 has remarkably low complementary to CCN2 and is found in the IGFBD domain. This positive effect of CCN3p37 and CCN3p38 was also found when examined during the immunohistochemical staining assay. CCN3p37 (FIG. 10A) and CCN3p38 (FIG. 10B) were able to block the redistribution and new synthesis of CCN2 in a dose-response manner indicating an effect on both production and activity, and appeared to also block the transition to a fibroblast-type cell, and important factor in the transition of cells to a phenotype thought to be important in the generation and progression of fibrosis in many organ systems. A similar effect on collagen type I was observed and occurred with both CCNp37 (FIG. 11A) and CCNp38 (FIG. 11B). The present invention therefore demonstrates for the first time, a method to block CCN2 synthesis and activity, cell binding or adhesion to CCN2, collagen accumulation, mesangial cell transition to a fibroblast-type cell and thus fibrosis, using unique small peptide s from very limited selective regions of the full-length CCN3 protein. Consequently, the CCN3 peptide of the present invention may be also used to block CCN2 mediated stimulation of cancer cell growth and to promote wound healing with minimal scarring. Since CCN2 is well-known as a key factor in the progression of a number of diseases, the ability to block this factor by such peptides has far reaching therapeutic applications. It was unexpected finding that one region with near total complementary and one different region with little or no complementary were both effective at blocking adhesion, CCN2 activity, adhesion and collagen activity. This could not be predicted.

One of the potential uses of the method in the present invention is for the treatment of fibrosis. The term "fibrosis" used in the present disclosure includes fibrosis and/or sclerosis and scarring since they are similar processes and all have been shown to have CCN2 as at least one causal factor. In the present disclosure, "fibrosis", "sclerosis" and "scarring" can be used interchangeably. The fibrosis can be associated with any organ capable of forming fibrosis; such as (but are not limited to) kidney, heart, liver, lungs, vasculature (including scleroderma, coronary arteries), skin, cervix, eye, gums, brain, and the peritoneum. The fibrosis can also be the result of one of the pathological conditions such as (but are not limited to) renal diseases, peritoneal dialysis, macular degeneration, periodontal disease, congestive heart failure, stroke and related ischemia and reperfusion injury, surgical and medical intervention procedures (e.g., balloon angioplasty, insertion of stents, catheters, grafts (including arterial and venous fistulas) and organ transplants) and unwanted post-surgical tissue or organ adhesions and scarring. The fibrosis can also be associated with increased cellular proliferation, for example, glomerular proliferative disease and vascular stiffness caused by cell proliferation, medial and intimal calcification. Other indications are associated with abnormal cellular proliferation, for example, cancer, particularly when growth or metastasis is related to upregulation of CCN2 expression, atherosclerosis, bone disease, osteophorosis, renal osteodystrophy, osteochondrodysplasia, osteitis fibrosa, osteoclastogenesis disease, vascular resistance, vascular calcification, tumorigenesis, and extracellular matrix disregulation. The pathology can be secondary to, the increased production/secretion and/or activity of TGF-β, wound healing, chronic kidney disease, intraglomerular hypertension, cancer cell growth, diabetes, hyperglycemia, hypertension, renal proliferataive disease, extracellular matrix disregulation disease or connective tissue disease Results from a study of the effect of CCN3 peptides on the growth of human chronic myelogenous leukemia cells FIG. 12 shows a bar graph of cellular proliferation of human chronic myelogenous leukemia cells (K562) as percent of the growth of the untreated control. In untreated cells (Control) and those pre-incubated with quantities of a commercial recombinant CCN3 (rCCN3c), or full length CCN3 made in our laboratory, represented by several preparations rCCN3 8, rCCN3 9, rCCN3 10, rCCN3 11, or the peptides CCN p37 or CCN p38 were allowed to grow, then proliferation measured by the CellTiter-Glo®Luminescent Cell Viability Assay Control untreated cells, or cells (McCallum, L et al, CCN3: *a key growth regulator in Chronic Myeloid*

Leukaemia, J Cell Commun Signal. 2009 June; 3(2): 115-124.). The latter is a homogeneous method of determining the number of viable cells in culture based on quantitation of the ATP present, an indicator of metabolically active cells. Our results showed that the commercially produced full length CCN3 produces an approximate 35% reduction in growth and/or viability over the period tested. In comparison, CCN3p37 produces 15-20% inhibition and CCN3p38 approximately 40% inhibition of cell growth. Thus the activity was greater than the full-length CCN3.

As an additional aspect, the invention includes kits which comprise one or more pharmaceutical formulations for administration of CCN3 peptides to a patient packaged in a manner which facilitates their use for administration to subjects. In one embodiment, such a kit includes pharmaceutical formulation described herein (e.g., a composition comprising a CCN3 peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (i.e., almost none). In one embodiment, the kit contains a first container having the CCN3 peptide composition and a second container having a physiologically acceptable reconstitution solution for the composition. In one aspect, the pharmaceutical formulation is packaged in a unit dosage form. The kit may further include a device suitable for administering the pharmaceutical formulation according to a specific route of administration. Preferably, the kit contains a label that describes use of the pharmaceutical formulations.

The present invention further provides administering the CCN3 peptides to a human subject through a route of administration including intravenous, intramuscular, nasal, topical, vaginal, anal, transdermal, inhalation, oral, bucal, intraperitoneal, intraosseous and combinations of the same. The transdermal route of administration includes transdermal patch or transdermal electrophoresis. It should also be understood that the CCN3 peptide can be modified by attaching a carrier molecule or entity, as is well known in the art, to protect the peptide from degradation, to target the peptide to a desired location in the human, to control the rate of delivery. Suitable carrier molecules include, but are not limited to, glycol groups, polyethylene glycol (PEG), proteins, including serum proteins. The present invention contemplates using excipients that are used in the pharmaceutical industry for the prescribed routes of delivery set forth above. The present invention contemplates modifying the CCN3 peptide to increase its stability, shelf life, half life in vivo, targeting within the body, to improve its attachment to a cell of interest or entry into the cell of interest.

In one preferred form of the invention, the CCN3 peptides can be used in stem cell treatment formulations by adding the peptides to cord blood, or bone marrow isolates to generate therapeutic stem cells ex vivo. Also, it could be speculated that such treatment in vivo might enhance the activity of naturally occurring stem cells, for better recovery from serious injury including ischemic heart disease, fibrosis, heart and liver failure among others.

The present invention provides for delivering an effective amount of the CCN3 peptides which can be determined by methods such as dose titration or other techniques known to those skilled in the art and can include dosages within the range of 0.1 nanomolar to 1 micromolar or approximately 0.1 nanogram per milliter to 1 microgram per milliliter. Concentrated amounts may also be required depending on the delivery form used.

The practice of the present invention will employ and incorporate, unless otherwise indicated, conventional techniques of cell biology, cell culture, molecular biology, microbiology, genetic engineering and immunology, which are within the skill of the art. While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

I claim:

1. A CCN3 peptide comprising a cysteine-substituted CCNp37 (SEQ ID NO 37), a cysteine-substituted CCNp38 (human) (SEQ ID NO 56) or a cysteine-substituted CCNp38 (mouse) (SEQ ID NO 38), wherein the native cysteine amino acids are substituted by an amino acid selected from the group consisting of serine, alanine, glycine, S-methylated cysteine or a combination thereof.

2. The CCN3 peptide of claim 1 wherein the cysteine-substituted CCNp37 (SEQ ID NO 37) comprises the native CCNp37 sequence with the native cysteine amino acids substituted with serine.

3. The CCN3 peptide of claim 1 wherein the cysteine-substituted CCNp38 (human) (SEQ ID NO 56) comprises the native CCNp38 (human) sequence (SEQ ID NO 51) with the native cysteine amino acids substituted with serine.

4. The CCN3 peptide of claim 1 wherein the cysteine-substituted CCNp38 (mouse) (SEQ ID NO 38) comprises the native CCNp38 (mouse) sequence (SEQ ID NO 49) with the native cysteine amino acids substituted with serine.

5. The CCN3 peptide of claim 1 wherein the CCN3 peptide is contained within a stem cell formulation.

6. A CCN3 peptide consisting essentially of a native mouse and a native human amino acid CCNp37 (respectively SEQ ID NOs 48 and 50), a native CCNp38 (human) (SEQ ID NO 51), and a native CCNp38 (mouse) (SEQ ID NO 49).

* * * * *